United States Patent
Kato et al.

(10) Patent No.: US 11,810,293 B2
(45) Date of Patent: Nov. 7, 2023

(54) INFORMATION PROCESSING DEVICE, INFORMATION PROCESSING METHOD, AND COMPUTER PROGRAM

(71) Applicant: EIZO Corporation, Hakusan (JP)

(72) Inventors: Yu Kato, Hakusan (JP); Masafumi Higashi, Hakusan (JP); Reo Aoki, Hakusan (JP); Mamoru Ogaki, Hakusan (JP); Ikumi Arai, Hakusan (JP); Noriyuki Hashimoto, Hakusan (JP); Naoaki Hirata, Hakusan (JP)

(73) Assignee: EIZO Corporation, Hakusan (JP)

( * ) Notice: Subject to any disclaimer, the term of this patent is extended or adjusted under 35 U.S.C. 154(b) by 560 days.

(21) Appl. No.: 17/056,876

(22) PCT Filed: Feb. 20, 2019

(86) PCT No.: PCT/JP2019/006364
§ 371 (c)(1),
(2) Date: Nov. 19, 2020

(87) PCT Pub. No.: WO2019/225084
PCT Pub. Date: Nov. 28, 2019

(65) Prior Publication Data
US 2021/0158513 A1    May 27, 2021

(30) Foreign Application Priority Data

May 23, 2018  (JP) ................. 2018-098989

(51) Int. Cl.
*G06T 7/00*    (2017.01)
*G06T 7/62*    (2017.01)

(52) U.S. Cl.
CPC .............. *G06T 7/0012* (2013.01); *G06T 7/62* (2017.01); *G06T 2207/30068* (2013.01)

(58) Field of Classification Search
CPC ................ G06T 7/0012; G06T 7/62; G06T 2207/30068; G06T 7/11;
(Continued)

(56) References Cited

U.S. PATENT DOCUMENTS 8,600,126 B2 * 12/2013 Morita .............. G06T 7/11
382/128
2009/0097730 A1    4/2009 Kasai et al.
(Continued)

FOREIGN PATENT DOCUMENTS

CN    101664316 A    3/2010
CN    101849836 A    10/2010
(Continued)

OTHER PUBLICATIONS

Office Action dated Dec. 22, 2021 in India Patent Application No. 202017054336; 5 pgs.
(Continued)

*Primary Examiner* — Jerome Grant, II
(74) *Attorney, Agent, or Firm* — Maier & Maier, PLLC

(57) ABSTRACT

The present invention has been made in view of the foregoing, and an object thereof is to provide an information processing device capable of appropriately determining a necessity of the ultrasonography even when a high-density mammary gland area exists in a narrow area. The present invention provides an information processing device comprising: a mammary gland area extractor configured to extract a mammary gland area in a mammography image; a mammary gland pixel detector configured to detect a mammary gland pixel in the mammary gland area; and a mammary gland density calculator configured to calculate a mammary gland density based on a ratio of the mammary
(Continued)

gland pixels to the mammary gland area, wherein the mammary gland area is a narrower area than an entire breast in the mammography image.

19 Claims, 21 Drawing Sheets

(58) Field of Classification Search
CPC ..... G06T 2207/10116; G06T 2207/20081; G16H 30/40; G16H 50/20; G16H 50/30; A61B 6/5217; A61B 8/0825; A61B 8/5223; A61B 6/502; A61B 5/0033; A61B 5/0091
USPC ........................................................ 382/128
See application file for complete search history.

(56) References Cited

U.S. PATENT DOCUMENTS

| | | |
|---|---|---|
| 2009/0324049 A1 | 12/2009 | Kontos et al. |
| 2010/0246924 A1 | 9/2010 | Morita |
| 2015/0030122 A1 | 1/2015 | Gorshkov et al. |
| 2015/0036906 A1 | 2/2015 | Kim et al. |
| 2015/0070385 A1 | 3/2015 | Ishizu et al. |
| 2015/0213302 A1 | 7/2015 | Madabhushi et al. |
| 2017/0221201 A1 | 8/2017 | Chang et al. |
| 2017/0345223 A1 | 11/2017 | Ishizu et al. |

FOREIGN PATENT DOCUMENTS

| | | | |
|---|---|---|---|
| CN | 103908258 A | 7/2014 | |
| CN | 107123110 A | 9/2017 | |
| CN | 107958453 A | 4/2018 | |
| EP | 2 366 332 A1 | 9/2011 | |
| JP | 2001-238868 A | 9/2001 | |
| JP | 2005065855 * | 3/2005 | .............. A61B 6/00 |
| JP | 2005065855 A | 3/2005 | |
| JP | 2005065857 A | 3/2005 | |
| JP | 2005-87470 A | 4/2005 | |
| JP | 2006-340835 A | 12/2006 | |
| JP | 2007236804 A | 9/2007 | |
| JP | 2009-072410 A | 4/2009 | |
| JP | 2009100926 A | 5/2009 | |
| JP | 2009268726 * | 11/2009 | .............. A61B 6/00 |
| JP | 2015-054051 A | 3/2015 | |
| JP | 2015-167829 A | 9/2015 | |
| JP | 2016-158963 A | 9/2016 | |
| JP | 2016-206693 A | 12/2016 | |
| KR | 20110039896 A | 4/2011 | |
| KR | 20170095012 A | 8/2017 | |
| RU | 2008125298 A | 12/2009 | |
| WO | 2012090472 A1 | 7/2012 | |
| WO | 2015062903 A1 | 5/2015 | |

OTHER PUBLICATIONS

X. Zhou et al. "Automated segmentation of mammary gland regions in non-contrast torso CT images based on probabilistic atlas." SPIE Digital Library. 2007. vol. 6512. 8 pages. XP040237478.
Extended European Search Report dated Mar. 9, 2021, in connection with corresponding EP Application No. 19807152.4; 9 pages.
Office Action dated May 23, 2023, in corresponding Chinese Application No. 201980030523.1, 15 pages.
International Search Report dated May 14, 2019 in corresponding International Application No. PCT/JP2019/006364; 3 pages.
Jonathan Long et al., "Fully Convolutional Networks for Semantic Segmentation", IEEE Transactions on Pattern Analysis and Machine Intelligence, vol. 39, Issue: 4, Apr. 1, 2017, 10 pages.
Japanese Office Action dated Dec. 18, 2020, in connection with corresponding JP Application No. 2020-521028 (6 pp., including machine-generated English translation).
Kiyoshi Namba, "5. Latest Technologies and Topics in Software Usefulness and Future Prospects of Quantitative Breast Density Assessment Software", Innervision, Aug. 2017, pp. 38-41.
Takayoshi Uematsu, "Thinking about Dense Breast: Current Status of Dense Breast Response in Japan", Journal of Japan Association of Breast Cancer Screening, Japan Association of Breast Cancer Screening, 2016, 25(3) Oct, pp. 205-210.

* cited by examiner

FIG.14    FIRST ADDITIONAL DATA D1(HORIZONTAL IMAGE DATA D11)
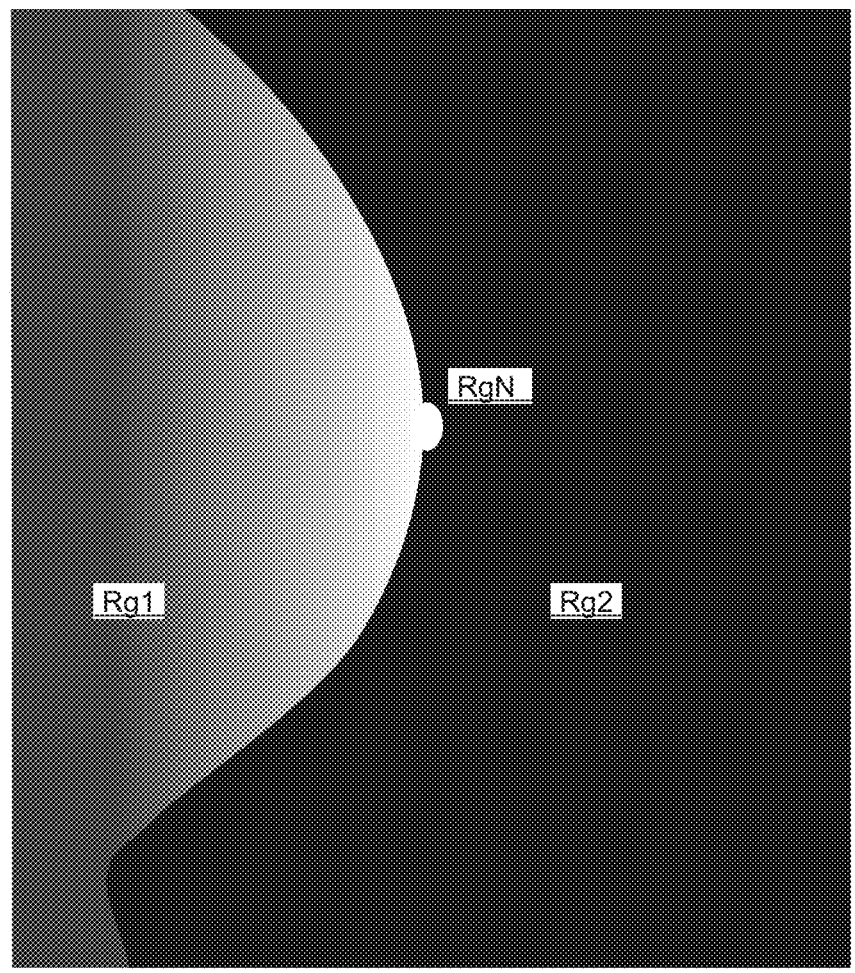
  GRADATION VALUE

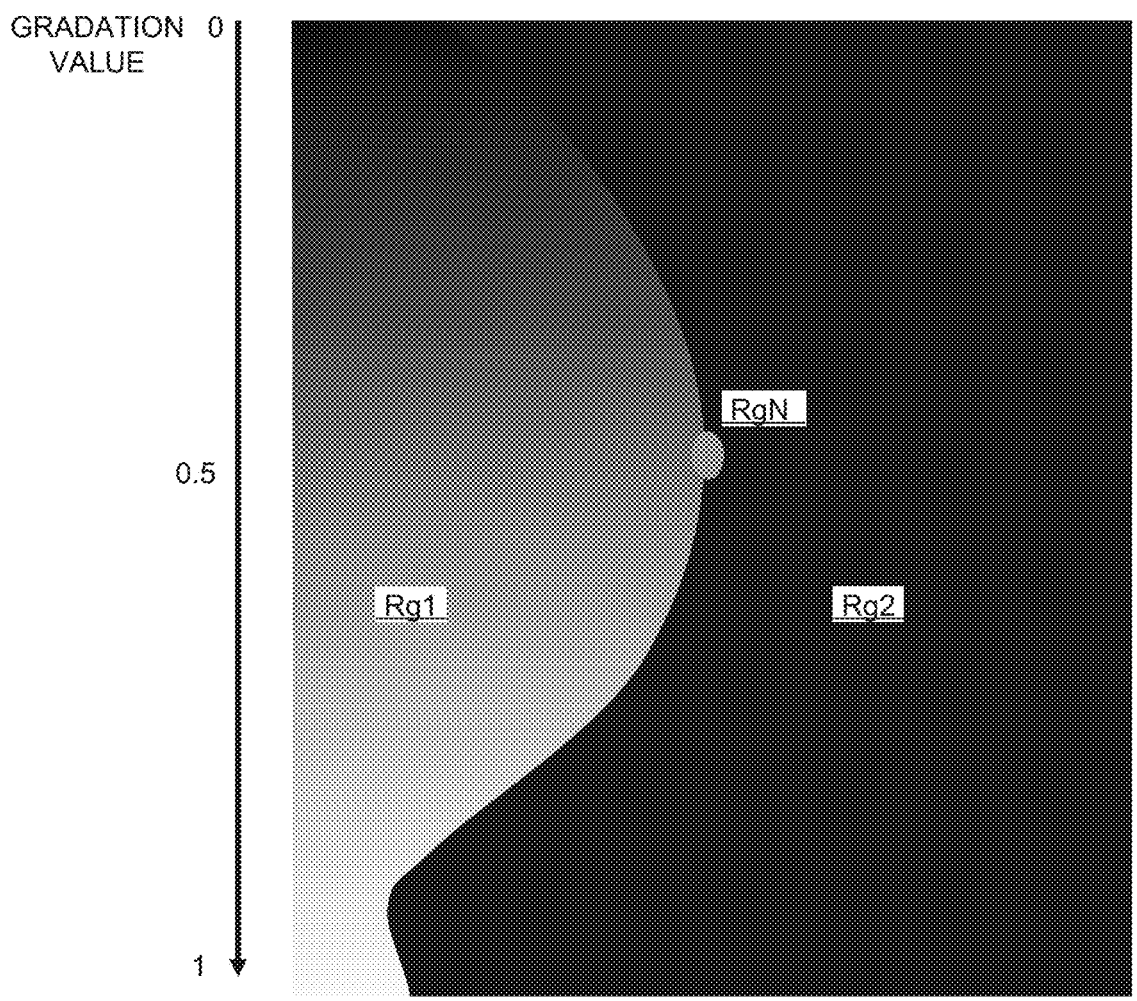

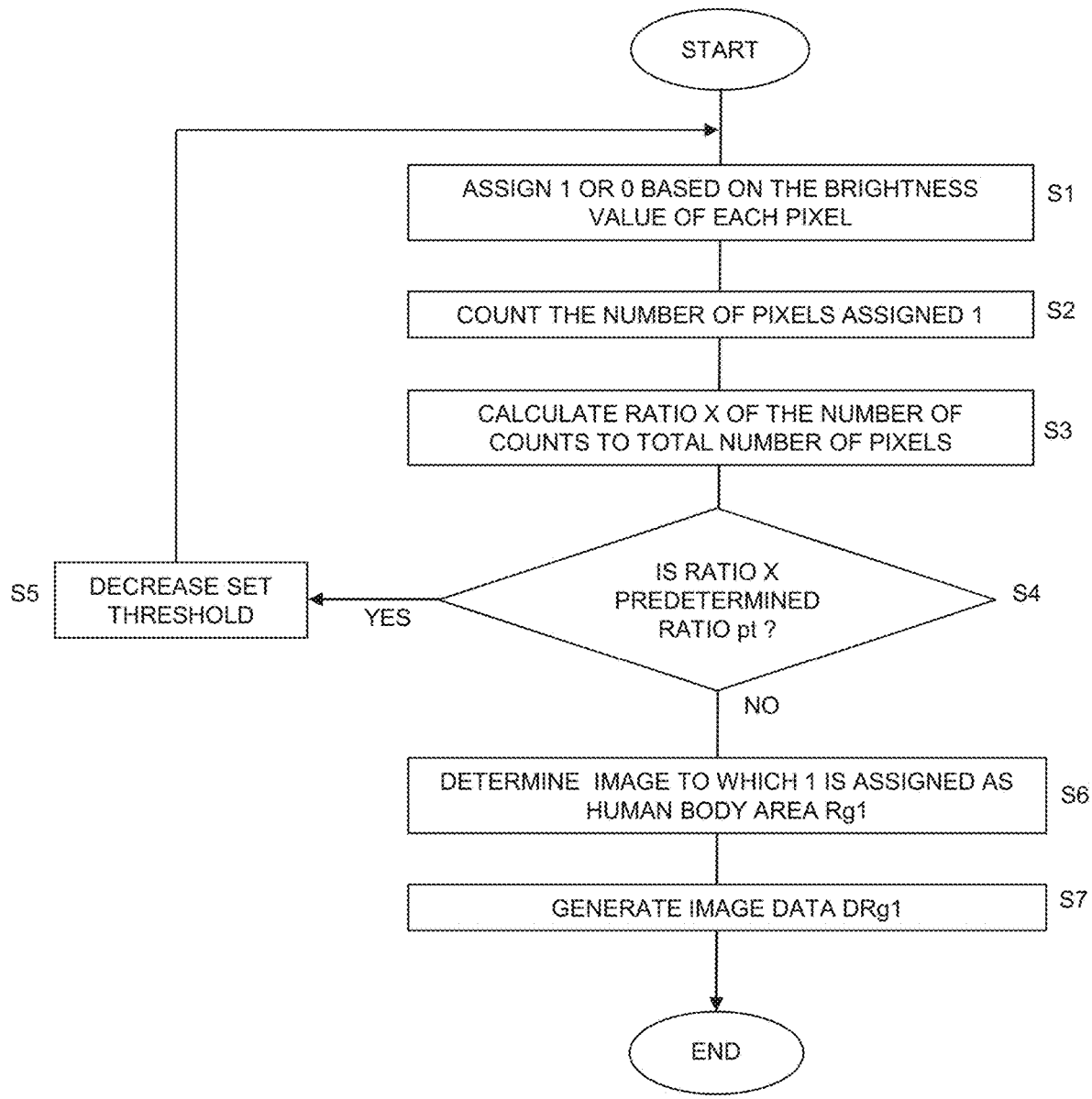

INFORMATION PROCESSING DEVICE, INFORMATION PROCESSING METHOD, AND COMPUTER PROGRAM

TECHNICAL FIELD

The present invention relates to an information processing device, an information processing method, and a computer program capable of calculating a mammary gland density in a mammography image.

BACKGROUND ART

Breast cancer screening basically uses mammography to determine calcification, tumors, and so on. However, when the density of the mammary gland in the breast is high, it may not be possible to accurately determine calcification, and so on (mostly in Japanese and young people). In these cases, more accurate screenings are performed by parallelly performing ultrasonography, which increases the screening cost and is not easily affected by the mammary gland. Thus, the interpretation doctors guide the examinees, when they judge that the mammary gland densities of the examinees are high based on the mammography images, to perform the ultrasonography diagnosis. At this time, there is no clear criterion for "the mammary gland density is high", and the criteria of the interpretation doctors are different, which is a problem.

Patent document 1 in paragraphs 59 to 62 discloses that a mammary gland ratio is calculated by dividing the mammary gland area by the breast area and the mammary gland density is determined based on the mammary gland ratio. The breast area is the entire area corresponding to the breast in the breast image, and the mammary gland area is an area, where the pixel value is equal to or greater than the threshold in the breast area.

CITATION LIST

Patent Literature

[Patent Literature 1] Japanese Unexamined Patent Application Publication No. 2016-158963

Non-Patent Literature

[Non-Patent Literature 1] Fully Convolutional Networks for Semantic Segmentation, IEEE Transactions on Pattern Analysis and Machine Intelligence (Volume: 39, Issue: 4, Apr. 1, 2017)

SUMMARY OF INVENTION

Technical Problem

In Patent Document 1, the mammary gland density is determined based on the mammary gland ratio calculated as described above. However, in such a determination method, the mammary gland ratio is calculated to be low when the high-density mammary gland area exists in a narrow area, which tends to lead to a diagnosis that the ultrasonography is unnecessary. However, even when the mammary gland area exists in the narrow area, the ultrasonography may be necessary in the case that the mammary gland area is dense, as the mammography cannot accurately determine calcification and so on. Thus, it is desirable to determine the necessity of the ultrasonography based on more appropriate criteria.

The present invention has been made in view of the foregoing, and an object thereof is to provide an information processing device capable of appropriately determining the necessity of the ultrasonography even when a high-density mammary gland area exists in a narrow area.

Solution to Problem

The present invention provides an information processing device comprising: a mammary gland area extractor configured to extract a mammary gland area in a mammography image; a mammary gland pixel detector configured to detect a mammary gland pixel in the mammary gland area; and a mammary gland density calculator configured to calculate a mammary gland density based on a ratio of the mammary gland pixels to the mammary gland area, wherein the mammary gland area is a narrower area than an entire breast in the mammography image.

In the present invention, the mammary gland area is the narrower area than the entire breast in the mammography image, and the mammary gland density is calculated based on the ratio of the mammary gland pixels to the mammary gland area. Thus, in the present invention, the information processing device provides information capable of appropriately determining the necessity of the ultrasonography even when the high-density mammary gland area exists in the narrow area.

Preferably, the mammary gland area extractor includes a mammary gland area probability calculator and a post-processor, the mammary gland area probability calculator is configured to calculate a probability that an area in the mammography image is the mammary gland area, and the post-processor is configured to extract the mammary gland area based on the probability.

Preferably, the post-processor includes a candidate pixel extractor and an area generator, the candidate pixel extractor is configured to generate a candidate pixel map by extracting, as a candidate pixel, a pixel having the probability that is equal to or greater than a first threshold, and the area generator is configured to form the mammary gland area by filling in a missing area with respect to the candidate pixel map.

Preferably, the mammary gland area probability calculator is configured to calculate the probability based on a learning model that outputs the probability when the mammography image is input.

Preferably, the mammary gland area probability calculator is configured to calculate the probability based on a learning model that outputs the probability when the mammography image and first additional data are input, and the first additional data is data relating to a position of a nipple in the mammography image.

Preferably, the first additional data is image data in which a pixel value of a human body pixel in the mammography image is corrected based on a position of a nipple pixel in the mammography image.

Preferably, the first additional data is the image data in which the pixel value of the human body pixel in the mammography image is corrected so that the pixel value of the human body pixel in the mammography image changes according to a linear distance between the nipple pixel and the human body pixel.

Preferably, the first additional data is the image data in which the pixel value of the human body pixel in the mammography image is corrected so that the pixel value of the human body pixel increases as the linear distance between the nipple pixel and the human body pixel decreases.

Preferably, the first additional data has first and second image data, the first image data is image data in which the pixel value of the human body pixel in the mammography image is corrected so that the pixel value of the human body pixel in the mammography image changes in a first direction of the mammography image, the second image data is image data in which the pixel value of the human body pixel in the mammography image is corrected so that the pixel value of the human body pixel in the mammography image changes in a second direction of the mammography image, and the first and second directions crosses.

Preferably, the first additional data is the image data in which the pixel value of the human body pixel in the mammography image is corrected so that the pixel value of the human body pixel increases as the linear distance in the first direction between the nipple pixel and the human body pixel decreases, and the second additional data is the image data in which the pixel value of the human body pixel in the mammography image is corrected so that the pixel value of the human body pixel increases from an upper side in the second direction to a lower side in the second direction.

Preferably, the mammary gland area probability calculator is configured to calculate the probability based on a learning model that outputs the probability when the mammography image and second additional data are input, and the second additional data is data indicating distribution of representative brightness value of the mammography image or brightness value of the mammography image.

Preferably, the second additional data is image data in which the brightness value of a human body pixel in the mammography image is corrected based on the representative brightness value or the distribution.

Preferably, the learning model is trained outside the information processing device in advance.

Preferably, the learning model is configured to be trainable in the information processing device.

Preferably, the mammary gland area probability calculator is configured to calculate the probability without removing a pectoralis major muscle area in the mammography image.

Preferably, the mammary gland pixel detector is configured to detect the mammary gland pixel in the mammary gland area based on the probability.

Preferably, the mammary gland pixel detector is configured to detect a pixel, as the mammary gland pixel, having the probability that is equal to or greater than a second threshold, and the probability of the mammary gland area is higher when the second threshold is used than when the first threshold is used.

Preferably, the mammary gland pixel detector is configured to detect the mammary gland pixel based on a brightness value of the mammary gland area.

According to another aspect of the embodiments provides an information processing method comprising: extracting a mammary gland area in a mammography image; detecting a mammary gland pixel in the mammary gland area; and calculating a ratio of the mammary gland pixels to the mammary gland area, wherein the mammary gland area is a narrower area than an entire breast in the mammography image.

According to another aspect of the embodiments provides a computer program causing a computer to execute an information processing method, the information processing method comprising: extracting a mammary gland area in a mammography image; detecting a mammary gland pixel in the mammary gland area; and calculating a ratio of the mammary gland pixels to the mammary gland area, wherein the mammary gland area is a narrower area than an entire breast in the mammography image.

BRIEF DESCRIPTION OF DRAWINGS

FIG. 14 is a schematic diagram showing an example of first image data in first additional data.

FIG. 15 is a schematic diagram showing an example of the second image data in the first additional data.

FIG. 17 is a float chart showing a process of generating image data DRg1.

DESCRIPTION OF EMBODIMENTS

Embodiments of the present invention will be described below. Any of features in the embodiments described below can be combined with one another. And the invention is established independently for each feature.

1. First Embodiment

Figure 1:
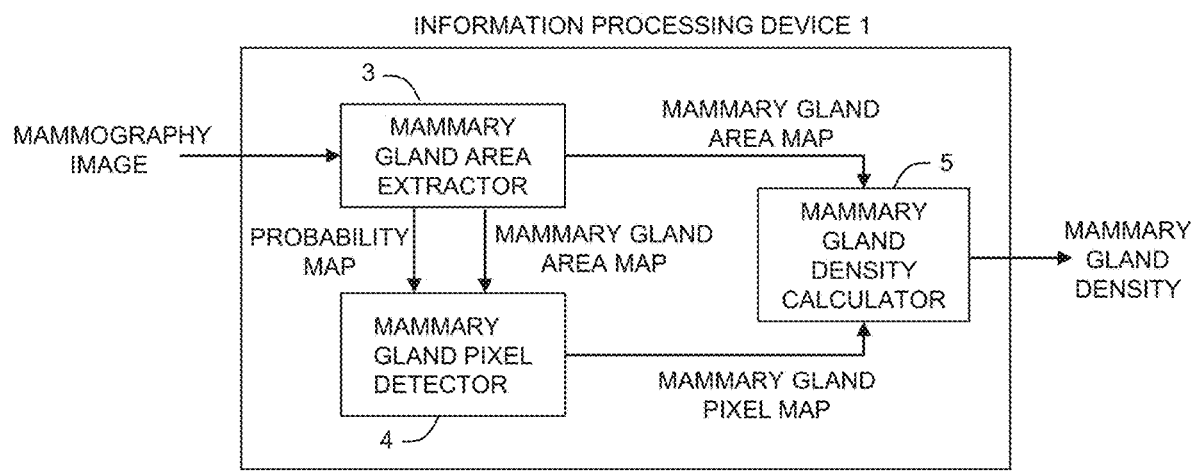
FIG. 1 is a block diagram showing a configuration of an information processing device 1 according to the first embodiment of the present invention.

An information processing device 1 of the first embodiment of the present invention will be described with reference to FIGS. 1 to 7. The information processing device 1 of the embodiment includes a mammary gland area extractor 3, a mammary gland pixel detector 4, and a mammary gland density calculator 5, as shown in FIG. 1.

Each of the above components may be realized by software or hardware. When realized by software, various functions can be realized by the CPU executing computer programs. The program may be stored in built-in memory or a non-transitory readable medium by a computer. Alternatively, the above functions are realized by reading the program stored in external memory using so-called cloud computing. When realized by hardware, the above functions can be performed by various circuits such as ASIC, FPGA, or DRP. The present embodiment deals with various information and concepts including this information, and the various information is a bit group of binary numbers having 0 or 1, and the various information is represented according to the level of signal value. And in the present embodiment, communications and calculations can be executed according to configurations of the above software and hardware.

1-1. Mammary Gland Area Extractor 3

Figure 3:
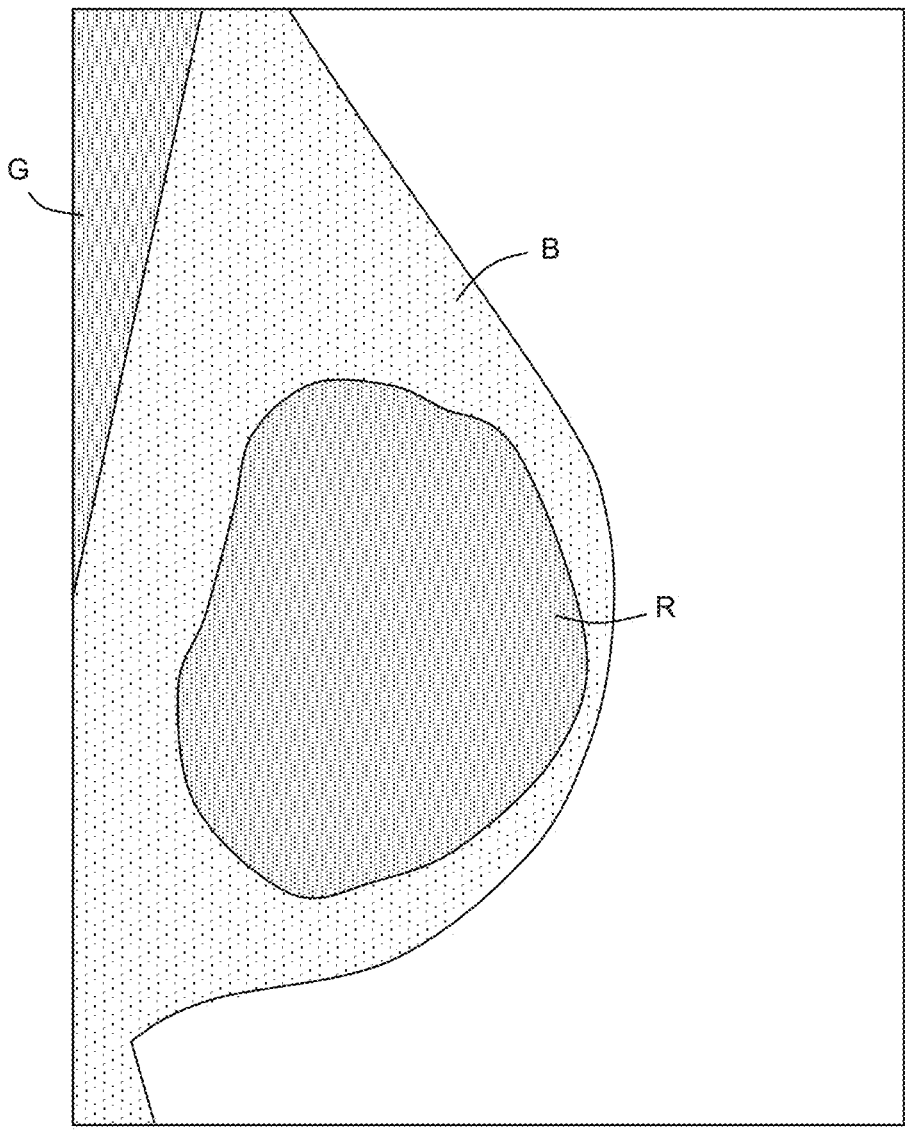
FIG. 3 is a schematic diagram showing an example of a mammography image.

The mammary gland area extractor 3 is configured to extract a mammary gland area R in a mammography image as shown in FIG. 3. The mammography image is a digital image having a large number of pixels. Each pixel has a brightness value. The mammography image usually includes the pectoralis major muscle area G and the breast area B. The pectoralis major muscle area G is the area corresponding to the pectoralis major muscle, and the breast area B is the area corresponding to the entire breast. Breast area B includes the mammary gland area R. The mammary gland area R is a narrower area than the mammary gland area B. The mammary gland area R includes mammary gland pixels and fat pixels. The mammary gland pixels are pixels corresponding to the mammary gland. The fat pixels are pixels corresponding to the fat, and are pixels other than the mammary gland pixels in the mammary gland area R. The mammary gland area R is the area that roughly encloses the mammary gland pixel.

In FIG. 3, for convenience of illustration, the mammary gland area R is surrounded by a solid line. But the actual mammography image has no solid line surrounding the mammary gland area R, and a part corresponding to the mammary gland is displayed in high brightness. Since the boundary of the part corresponding to the mammary gland is unclearly distributed like a cloud and it is difficult to uniquely define the boundary. Thus, the embodiment extracts the mammary gland area R based on the probability P that an area in the mammography image is the mammary gland area R. The solid lines showing the pectoralis major muscle area G and breast area B do not exist in the actual mammography image.

Figure 2:
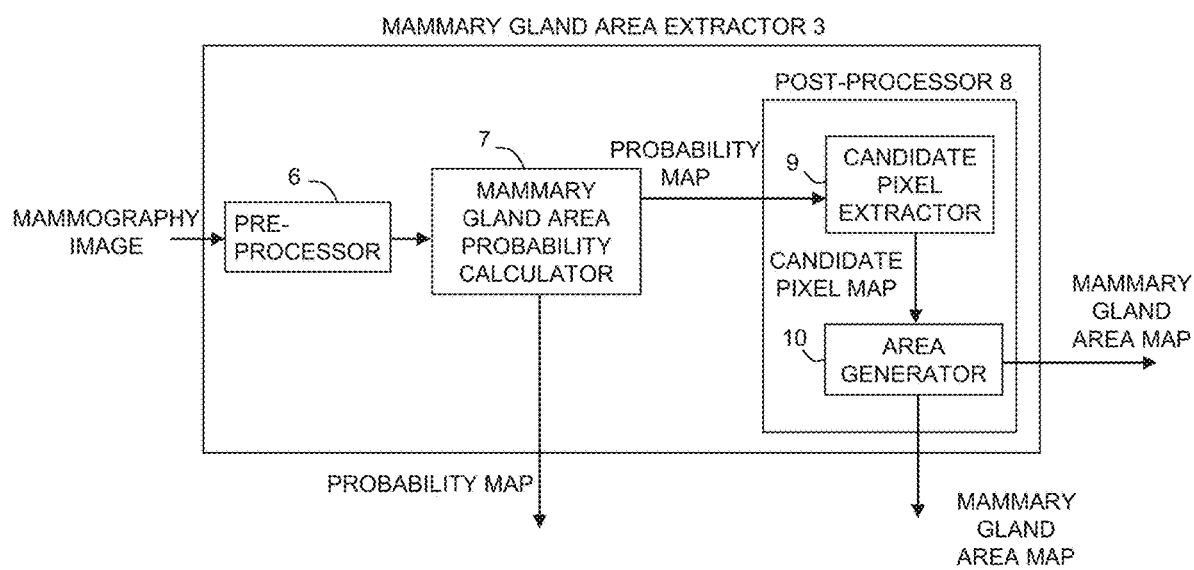
FIG. 2 is a block diagram showing a detailed configuration of a mammary gland area extractor 3 in FIG. 1.

As shown in FIG. 2, the mammary gland area extractor 3 includes a pre-processor 6, a mammary gland area probability calculator 7, and a post-processor 8. Hereinafter, each configuration will be described in detail.

<Pre-Processor 6>

The pre-processor 6 is configured to perform various preprocessing on the mammography image. The preprocessing is performed to bring the mammography image into an image suitable for processing in the mammary gland area probability calculator 7. The preprocessed image is also called the mammography image.

The pre-processor 6 includes a size adjustment part, a window level adjustment part, and a noise removing part. Part or all of the pre-processor 6 may be omitted if not needed.

Size Adjustment Part

The size adjustment part is configured to adjust the size of the mammography image. The resolution of the mammography image varies depending on the imaging equipment and settings. This means that the actual size (mm) per pixel differs depending on an input image. The size adjustment part resizes the mammography image to, for example, 0.2 mm per pixel to eliminate fluctuations in detection accuracy due to a size difference per pixel.

Window Level Adjustment Part

The window level adjustment part is configured to adjust the window level of the mammography image. Window level adjustment is a process for improving the contrast in a specific gradation range of an image having a wide range of gradation values. The visibility of the mammography image can be improved by adjusting the window level. As a result, extraction accuracy of the mammary gland area R can be improved.

Noise Removing Part

The noise removing part is configured to remove noise from the mammography image. Some mammography images may include the pixels that reduce the extraction accuracy of the mammary gland area R. The noise removing part removes them as noise. Examples of noise include artificial labels and pectoralis major muscle area G. The artificial label is artificially attached and can be removed by masking. The pectoralis major muscle area G can be removed by known area expansion methods. However, in the embodiment, since the mammary gland area R can be extracted even when the mammography image includes the pectoralis major muscle area G, the pectoralis major muscle area G does not have to be treated as noise.

The order of the size adjustment, the window level adjustment, and the noise removal may be appropriately changed.

<Mammary Gland Area Probability Calculator 7>

The mammary gland area probability calculator 7 is configured to calculate the probability P that the area in the mammography image is the mammary gland area R.

Commonly, in the mammography images, the brightness values of the pectoralis major muscle area G and the mammary gland area R (especially the mammary gland pixel) are higher than that of other areas (in other words, X-ray transmittance is lower than that of other areas). The brightness values of the pectoralis major muscle area G and the mammary gland area R are similar, and it is difficult to distinguish between the pectoralis major muscle area G and the mammary gland area R by brightness values. Thus, the information processing device 1 of the embodiment calculates the probability P indicating whether each pixel in the mammography image is the mammary gland area R, and extracts the mammary gland area R based on the probability P. Since the probability P is low in the pectoralis major muscle area G and is high in the mammary gland area R, it is possible to improve the detection accuracy of the mammary gland area R by extracting the mammary gland area R based on the probability P. Besides, the probability P can be calculated without removing the pectoralis major muscle area in the mammography image. The probability P is expressed by a value in the range of 0 to 1, for example. And the higher this value, the higher the probability P that the corresponding pixel is the mammary gland area.

The probability P can be calculated based on the learning model that outputs the probability P when the mammography image is input.

The learning model allows the model to be trained using a large number of the training data (a set of known input data and correct answer data) and the learning model is the model that makes future output predictable. In the embodiment, the input data of the training data is the mammography image. The correct answer data is data in which the values of the pixels in the area, which is determined as the mammary gland area by the doctor, are set to 1, and the values of the other pixels are set to 0.

In the embodiment, the learning model (machine learning model) is a FCN (Fully Convolutional Network), which is a type of convolutional neural network. Details of FCN are disclosed in Non-Patent Literature 1.

Figure 4:
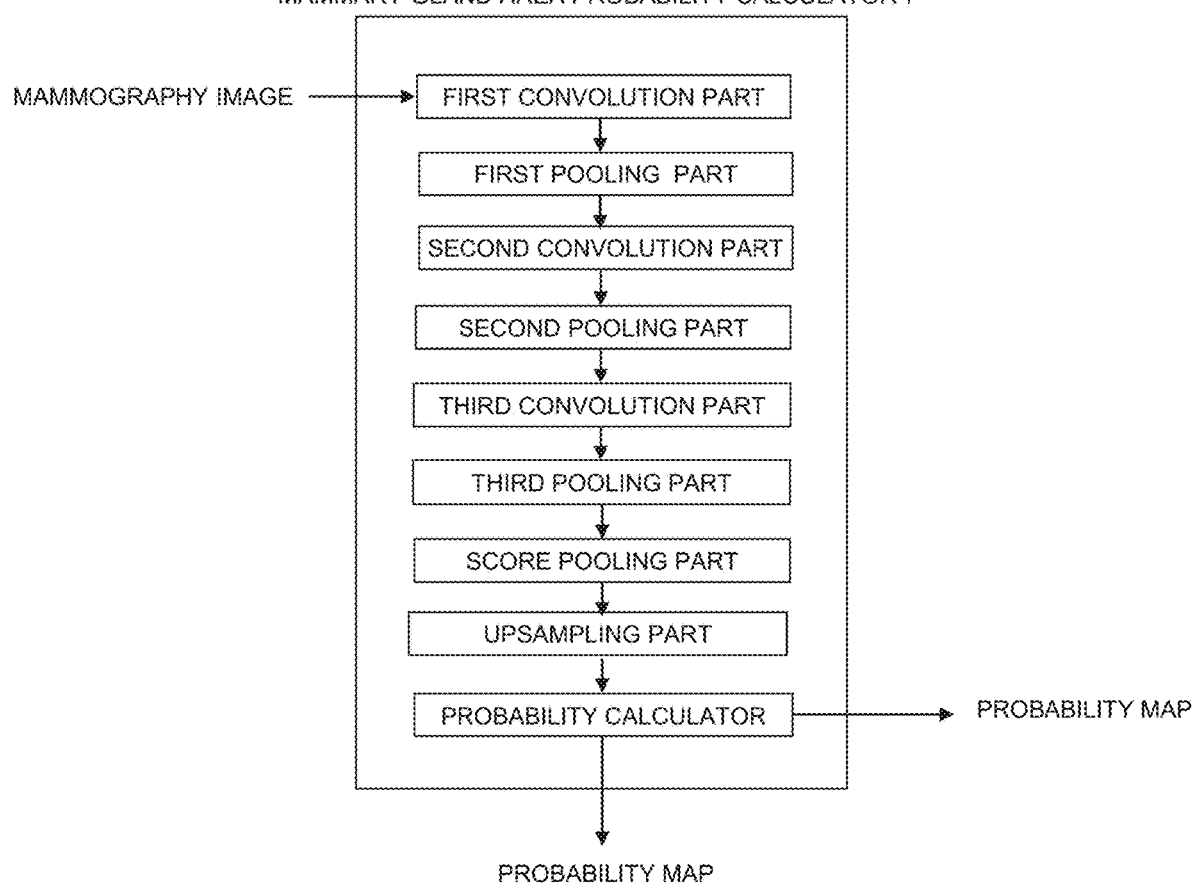
FIG. 4 is a block diagram showing a detailed configuration of a mammary gland area probability calculator 7 in FIG. 2.

As shown in FIG. 4, an example of FCN in the mammary gland area probability calculator 7 includes a first convolution part, a first pooling part, a second convolution part, a second pooling part, a third convolution part, a third pooling part, a score pooling part, an upsampling part, and a probability calculation part. The FCN configuration may be appropriately changed.

The first to third convolution parts include two-layer, two-layer, and three-layer neural networks, respectively. The number of neurons in each layer of the first to third convolution parts is 64,128,256. In the first to third convolution parts, the convolution processing is performed with a 3×3 pixel filter.

In the first to third pooling parts, pooling processes are performed to obtain maximum value in 2×2 pixels.

The score pooling part includes a neural network with 2 neurons, and convolution processing is performed with a 1×1 pixel filter in the score pooling part.

In the upsampling part, the number of pixels reduced by the pooling process is returned to the number of pixels in the mammography image. The upsampling part includes the neural network with two neurons. In the upsampling part, the number of pixels reduced by the pooling process is returned to the number of pixels in the mammography image by performing processing such as the convolution processing with a 16×16 pixel filter on pixel data in which a pixel with a value of 0 are appropriately inserted between adjacent pixels.

The probability calculation part is configured to calculate the probability P for each pixel by softmax function and outputs a probability map. The probability map has pixels corresponding to the pixels of the mammography image. Each pixel of the probability map has a probability P.

Learning can be performed by repeating the following processes of (1) to (2).

(1) Acquiring the output data by binarizing the probability P, which is obtained by inputting the input data having the training data, with reference to the threshold Th. The threshold Th is set to, for example, 0.5.

(2) Changing a weight coefficient of the filter by calculating an error based on the output data and the correct answer data, and by backpropagating this error.

The above learning may be performed in advance outside the information processing device 1. In this case, the information processing device 1 may be configured to calculate a mammary gland area probability using the weight coefficient obtained by external learning. The weight coefficient may be stored in a memory of the information processing device 1, or the weighting coefficient stored in an external memory may be read out and used by the information processing device 1. Besides, the information processing device 1 may be capable of learning the weight coefficient.

<Post-Processor 8>

The post-processor 8 is configured to extract the mammary gland area R based on the probability P. The post-processor 8 includes a candidate pixel extractor 9 and an area generator 10.

Candidate Pixel Extractor 9

The candidate pixel extractor 9 is configured to generate a candidate pixel map by extracting pixels, whose probability P exceeds a first threshold, as candidate pixels, and is configured to output the candidate pixel map. The first threshold may be the same as or different from the threshold Th at the learning stage. The first threshold may be a fixed value or a value that can be changed by the users as appropriate. The candidate pixel map has pixels corresponding to the pixels of the probability map. In the candidate pixel map, the value of the pixel whose the probability P is greater than or equal to the first threshold is, for example, 1, and the value of the pixel whose the probability P is less than the first threshold is, for example, 0.

Figure 5:
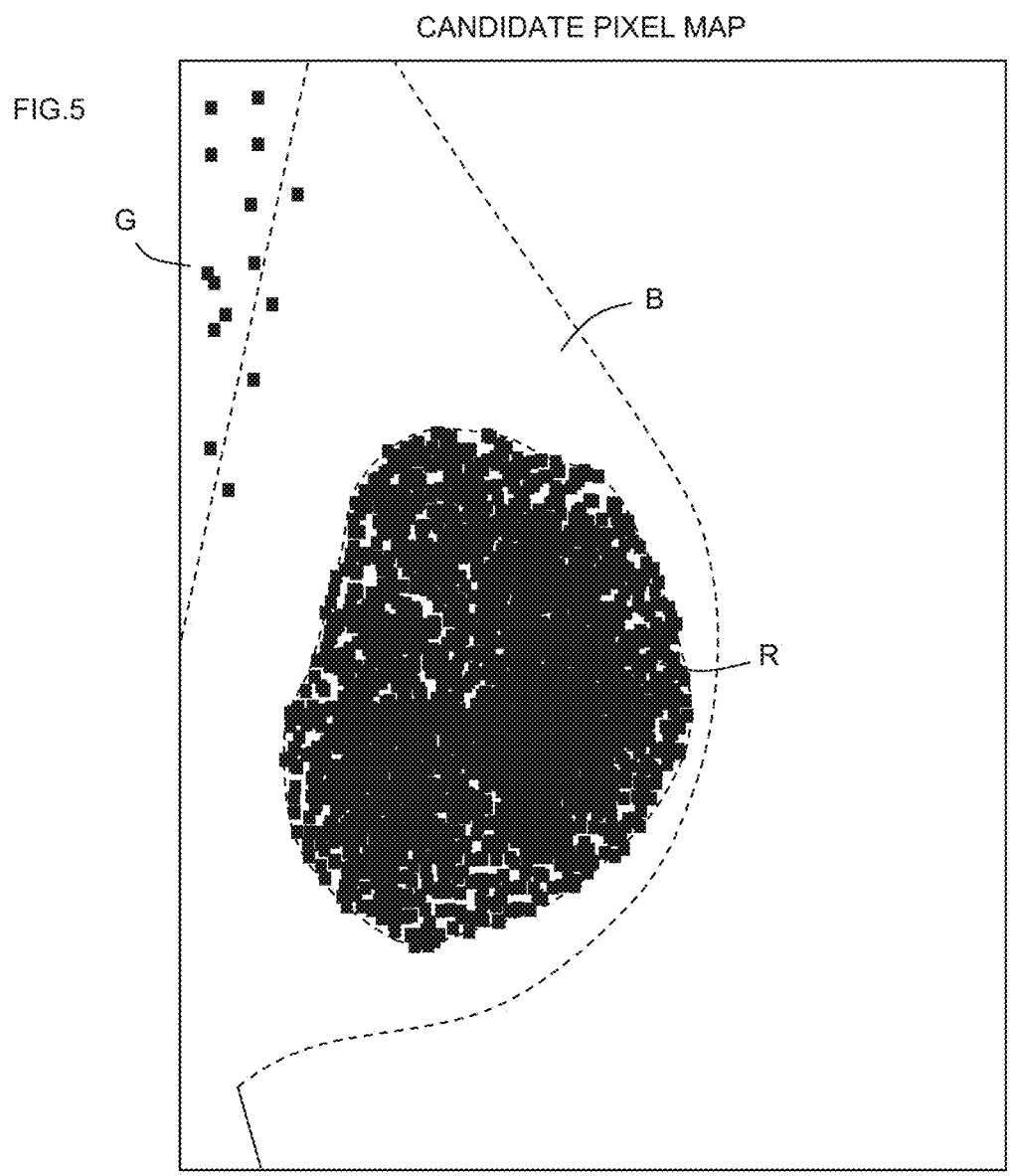
FIG. 5 is a schematic diagram showing an example of a candidate pixel map.

An example of the candidate pixel map is shown in FIG. 5. The candidate pixels are indicated by black dots. The boundaries of the pectoralis major muscle area G, the mammary gland area R, and the mammary gland area B are shown by dotted lines for reference. Regarding the candidate pixel map, a large number of the candidate pixels are extracted in the area corresponding to the mammary gland area R, and a small number of the candidate pixels are also extracted in the area corresponding to the pectoralis major muscle area G. A large number of the candidate pixels are concentrated in the area corresponding to the mammary gland area R, but there are missing areas (white area in the mammary gland areas R of FIG. 5) between the candidate pixels. Therefore, this mammary gland area R does not form one area.

Area Generator 10

The area generator 10 is configured to form the mammary gland area R by removing noise and filling in the missing areas with respect to the candidate pixel map.

Figure 6:
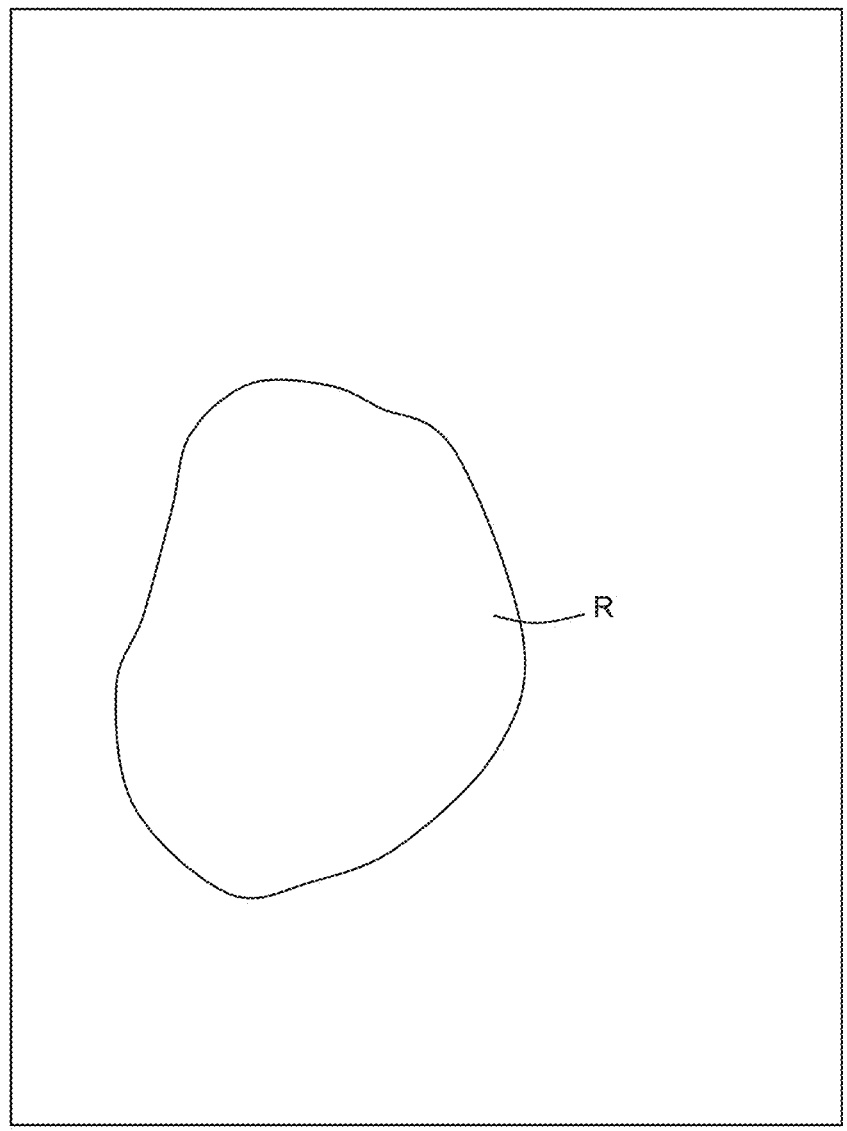
FIG. 6 is a schematic diagram showing an example of a mammary gland area map.

Specifically, the candidate pixel in the area corresponding to the pectoralis major muscle area G is regarded as noise and is removed by processing such as mask processing. Besides, for the area corresponding to the mammary gland area R, the missing areas are filled to form the mammary gland area R. The missing area may be filled in, for example, by filling in a space from the start point to the end point of each of the columns and rows. This gives the mammary gland area map as shown in FIG. 6. Since the mammary gland area R is formed in the area where the candidate pixels are concentrated, it is preferable to ignore the candidate pixels, far from the area where the candidate pixels are concentrated, as noise in the missing area filling step. For example, even when the start point of the column or the row is detected, the detected start point may be discarded and a new start point may be searched when a predetermined number or more of non-candidate pixels are consecutive after the start point is detected.

The noise removal step may be omitted by sufficiently learning the learning model so that the candidate pixel is not generated in the area corresponding to the pectoralis major muscle area G. Also, when the pectoralis major muscle area G is removed from the mammography image in advance, the noise removal step may be omitted. Furthermore, in the processing of filling in the missing area, the candidate pixels in the pectoralis major muscle area G and the candidate pixels that exist outside the pectoralis major muscle area G and outside the area where the candidate pixels are concentrated can be removed by ignoring the candidate pixels that are far from the area where the candidate pixels are concentrated. Therefore, it is possible to form the mammary gland area R in the missing area filling step without performing the noise removal step.

1-2. Mammary Gland Pixel Detector 4

The mammary gland pixel detector 4 is configured to detect the mammary gland pixel in the mammary gland area R. The mammary gland pixel detector 4 is configured to detect the mammary gland pixel in the mammary gland area R based on the probability P. The mammary gland pixel is a pixel whose probability P is greater than or equal to second threshold. The probability of the mammary gland area R is higher when the second threshold is used than when the first threshold is used. The mammary gland pixel detector 4 may detect the mammary gland pixel in the mammary gland area map extracted by the mammary gland area extractor 3.

More specifically, the mammary gland pixel detector 4 is configured to generate a mammary gland pixel map by extracting the pixel, whose probability P exceeds the second threshold, as mammary gland pixel, and is configured to outputs the mammary gland pixel map. The mammary gland pixel map has the pixel corresponding to the pixel of the probability map. In the mammary gland pixel map, the value of the pixel whose probability P is greater than or equal to the second threshold is, for example, 1, and the value of the pixel whose probability P is less than the second threshold is, for example, 0.

Figure 7:
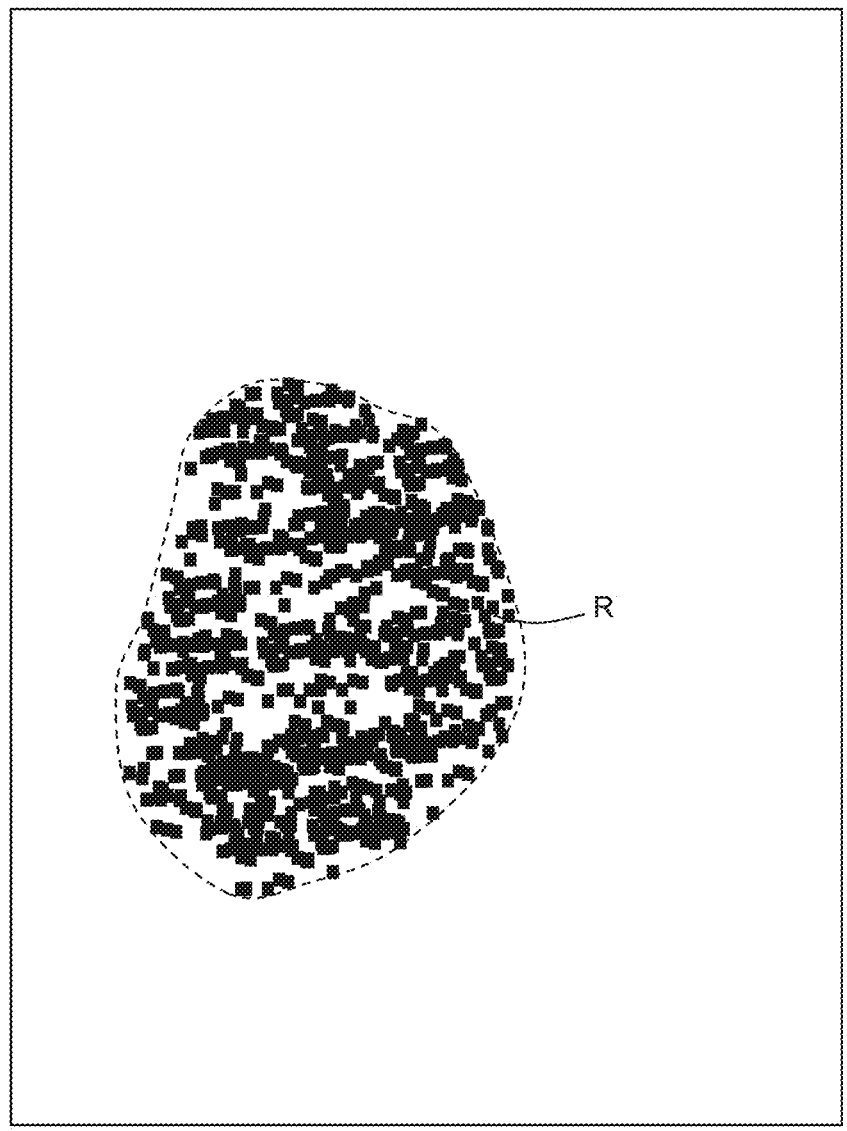
FIG. 7 is a schematic diagram showing an example of a mammary gland pixel map.

An example of the mammary gland pixel map is shown in FIG. 7. The mammary gland pixel is indicated by a black dot. The boundary of the mammary gland area R is shown by the dotted line for reference. Information on the mammary gland area R may be included in the mammary gland pixel map based on the mammary gland area R extracted by the mammary gland area extractor 3. As shown in FIG. 7, the mammary gland pixels are concentrated in the mammary gland area R. The number of mammary gland pixels is less than the number of the candidate pixels. The mammary gland pixel may exist outside the mammary gland area R. The mammary gland pixel outside the mammary gland area R may or may not be included as the mammary gland pixel when calculating a mammary gland density. In the case that when calculating the mammary gland density, the mammary gland pixel outside the mammary gland area R is not included as the mammary gland pixel, the calculation of the mammary gland density is performed with respect to the mammary gland pixel only in the mammary gland area map.

1-3. Mammary Gland Density Calculator 5

The mammary gland density calculator 5 is configured to calculate the mammary gland density based on a ratio of the mammary gland pixel to the mammary gland area R. More specifically, the mammary gland density calculator 5 counts the total number of pixels in the mammary gland area (total number of pixels in the mammary gland area) based on the mammary gland area map, and counts the number of mammary gland pixels based on the mammary gland pixel map. And the mammary gland density calculator 5 calculates the mammary gland density based on the following formula.

Mammary gland density (%)=100×(Number of the mammary gland pixels)/(Total number of pixels in the mammary gland area)

The mammary gland density calculated in this way is high when a high-density mammary gland area exists in the narrow area. Therefore, the configuration of the embodiment provides information that can appropriately determine the necessity of the ultrasonography even when the high-density mammary gland area exists in the narrow area.

The calculated mammary gland density can be used by displaying the calculated mammary gland density on the display part of the information processing device 1 or outputting the calculated mammary gland density to an external device from the information processing device 1.

2. Second Embodiment

Figure 8:
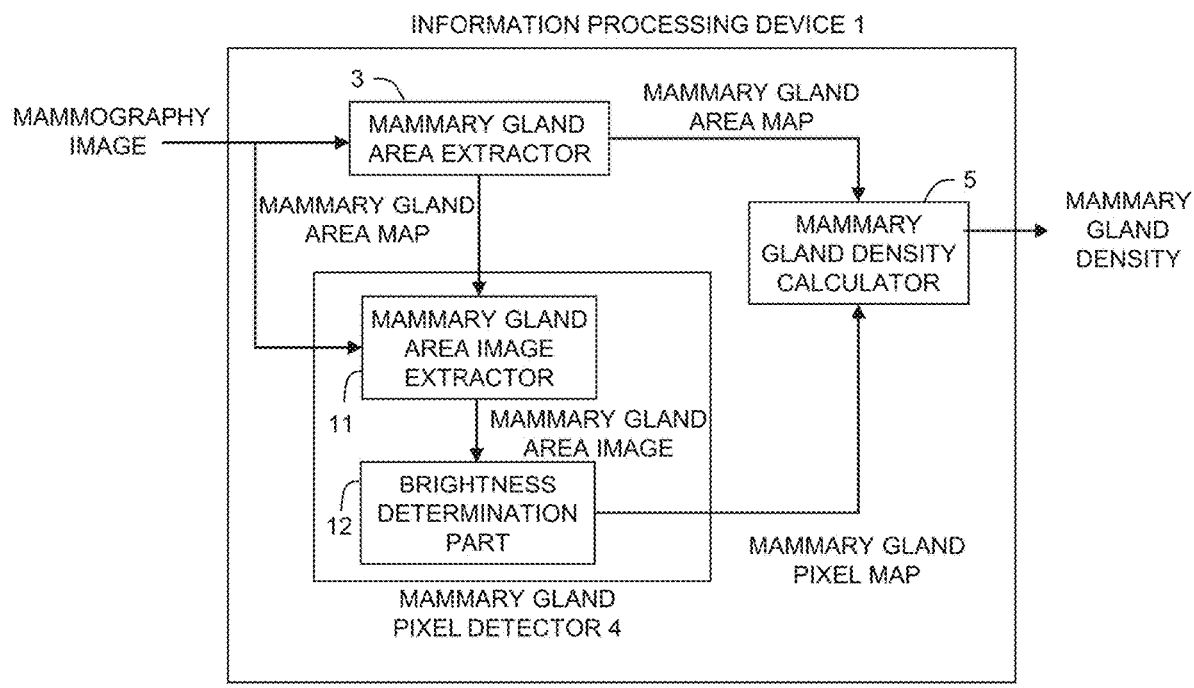
FIG. 8 is a block diagram showing a configuration of the information processing device 1 according to the second embodiment of the present invention.
Figure 9:
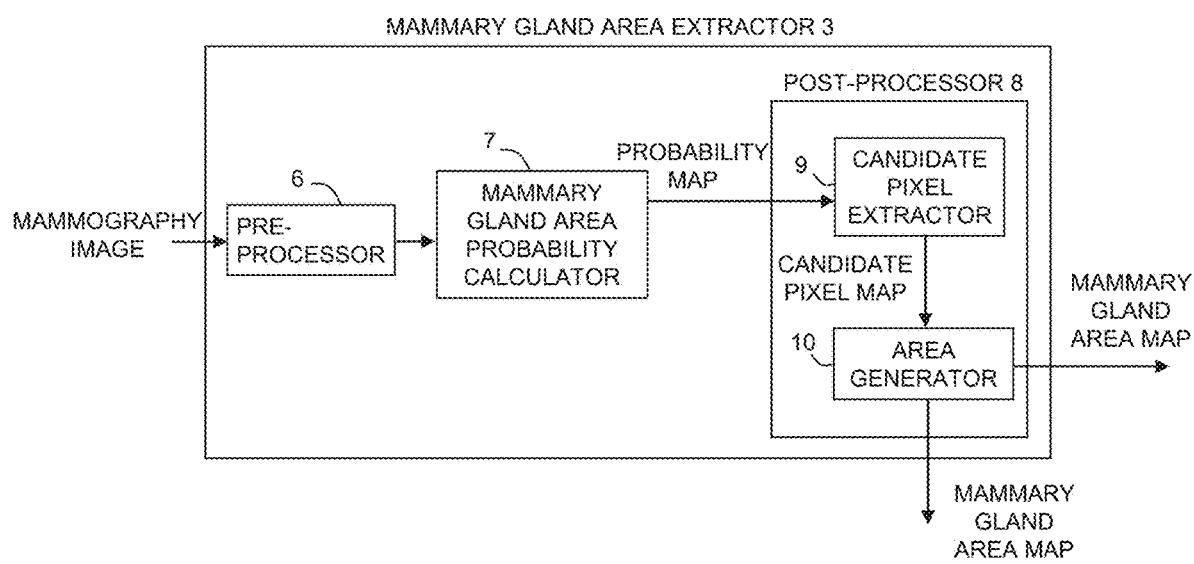
FIG. 9 is a block diagram showing a detailed configuration of the mammary gland area extractor 3 in FIG. 8.

The information processing device 1 of the second embodiment of the present invention will be described with reference to FIGS. 8 to 9. The information processing device 1 of the present embodiment is similar to the first embodiment, and the main difference is the configurations of the mammary gland pixel detectors 4. Hereinafter, the differences will be mainly described.

In the embodiment, the mammary gland pixel detector 4 is configured to detect the mammary gland pixel based on a brightness value of the mammary gland area R. The mammary gland pixel detector 4 includes a mammary gland area image extractor 11 and a brightness determination part 12.

The mammary gland area image extractor 11 is configured to extract the mammary gland area images based on the mammography image and mammary gland area map. The mammary gland area image only includes the image in the mammary gland area R.

The brightness determination part 12 is configured to detect the mammary gland pixel based on whether the brightness value of each pixel in the mammary gland area image is equal to or higher than a third threshold, and is configured to output the mammary gland pixel map. The third threshold may be set to a fixed value, or may be set based on various other known methods. The embodiment may use, for example, the mode methods that assume the bimodality of the histogram, the discriminant analysis methods that automatically determine the threshold, and adaptive threshold processing that locally changes the threshold, which is suitable for the embodiment.

The mammary gland area extractor 3 is the same as the first embodiment except that the mammary gland area extractor 3 outputs the mammary gland area map to the mammary gland pixel detector 4.

3. Third Embodiment

The information processing device 1 of the third embodiment of the present invention will be described with reference to FIGS. 10 to 17. The information processing device 1 of the first embodiment is configured to acquire the probability map based on the data of the mammography image. The information processing device 1 of the third embodiment is configured to acquire the probability map based on not only the mammography image but first and second additional data described later. The information processing device 1 of the third embodiment includes an additional data generator 30 configured to generate the first and second additional data in addition to the configurations of the information processing device of the first embodiment. Hereinafter, the differences between the first embodiment and the third embodiment will be mainly described.

In the third embodiment, a human body area Rg1 is an area corresponding to the human body in the mammography image D0. A human body pixel is a pixel in the human body area Rg1. The non-human body area Rg2 is an area corresponding to a part other than the human body in the mammography image D0. A nipple area RgN is an area corresponding to the nipple of the human body in the mammography image D0, and the nipple area RgN is included in the human body area Rg1. A nipple pixel is a pixel in the nipple area RgN.

3-1. Data Description

The information processing device 1 is configured to acquire the probability map based on the data of the mammography image (hereinafter, also simply referred to as the mammography image D0), the first additional data D1, and the second additional data D2. By using the first and second additional data D1 and D2, the information processing device 1 can acquire a more accurate probability map.

<First Additional Data D1>

Since the human body has many mammary glands near the nipple, a part near the nipple has a high probability that the part is the mammary gland. Thus, in the third embodiment, the mammary gland area extractor 3 is trained using data that reflects on the distance from the nipple, and the third embodiment makes the output (the probability map) of the mammary gland area extractor 3 more accurate. In the third embodiment, the data including the distance from the nipple is image data. Further, in the third embodiment, this image data is the image data in which the brightness value of the human body pixel in the mammography image is corrected. Since the pectoralis major muscle area G is located in the upper-left end side of the mammography image D0, the probability, indicating that the pixel in the upper-left end side of the mammography image D0 is the mammary gland, is low. Thus, in the third embodiment, the mammary gland area extractor 3 is trained by using the image data (the first additional data D1) that reflects on the distance from the pectoralis major muscle area G, and the third embodiment makes the output (the probability map) of the mammary gland area extractor 3 more accurate. When the output (the probability map) of the mammary gland area extractor 3 becomes more accurate, the accuracy of the candidate pixel map (see FIG. 5), the accuracy of the mammary gland area map (see FIG. 6), and the accuracy of the mammary gland pixel map (FIG. 7) are also improved. As a result, the mammary gland density calculator 5 can calculate the mammary gland density with higher accuracy. Therefore, the mammary gland area extractor 3 executes processes using the first additional data D1 that reflects on the distance from the nipple and the distance from the pectoralis major muscle area G.

Figure 12:
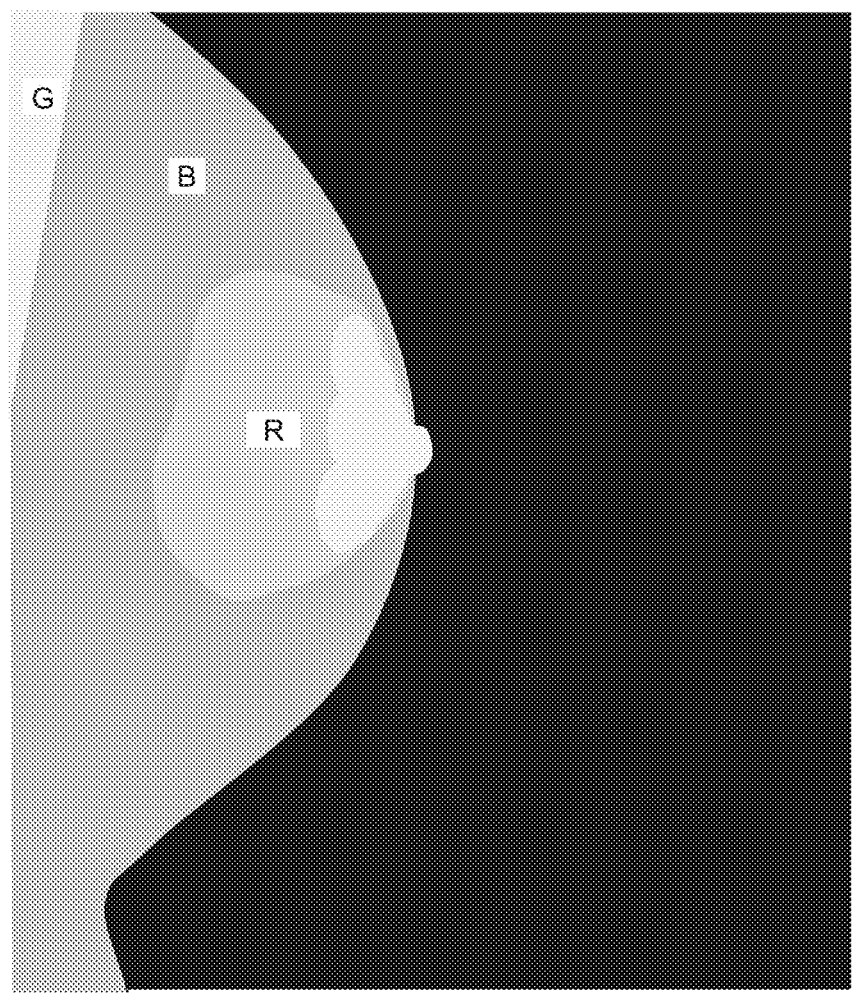
FIG. 12 is a schematic diagram of the mammography image input to the information processing device 1 of the third embodiment of the present invention.

As shown in FIG. 12, FIGS. 14, and 15, the first additional data D1 is the image data generated based on the mammography image D0. The first additional data D1 has first and second image data D11 and D12. The first and second image data D11 and D12 is data that reflects on both the distance between each pixel in mammography image D0 and the nipple area and the distance between each pixel in mammography image D0 and the pectoralis major muscle area.

First Image Data D11

As shown in FIGS. 12 and 14, the first image data D11 is the image data, which is corrected the brightness value of each human body pixel in mammography image D0, based on the position (coordinates) of the pixel in the nipple area RgN in the mammography image D0. In the third embodiment, the brightness value of each human body pixel in the first image data is based on the first direction distance between the position (coordinates) of the nipple area RgN and each human body pixel in the human body area Rg1 in the mammography image D0. That is, the first image data D11 is the image data in which the brightness value of each human body pixel in the mammography image D0 is corrected so that the brightness value of the human body pixel in mammography image D0 changes according to the first direction distance between the nipple area RgN and each human body pixel. In the third embodiment, the first direction of the first direction distance is the horizontal direction.

In the first image data D11 of the third embodiment, the brightness value of each human body pixel in the mammography image D0 is corrected so that the brightness value of each human body pixel increases as the first direction distance decreases.

In other words, since the first direction distance of the nipple area RgN of the first image data D11 is the minimum, the brightness value of this nipple area RgN is the maximum. Also, since the first direction distance of a left end part of the first image data D11 is the maximum, the brightness value of the human body pixel of the left end part is the minimum. Furthermore, the brightness value of the human body pixel decreases monotonically from a side of the nipple area RgN of the first image data D11 to a side of the left end part of the first image data D11. The brightness value of the human body pixel may or may not decrease in proportion to this first direction distance. In the third embodiment, the gradation value of the nipple area RgN of the first image data D11 is 1, and the gradation value of the human body pixel of the left end part of the first image data D11 is 0. In the third embodiment, the gradation value is normalized, the maximum value of the gradation value is 1, and the minimum value is 0. The maximum and minimum values of the brightness value are not limited to these values.

In the third embodiment, the brightness value of the human body pixel decreases monotonically from the side of the nipple area RgN of the first image data D11 to the side of the left end part of the first image data D11. However, the embodiment is limited to this. The brightness value of the human body pixel may turn to increase, from the side of the nipple area RgN of the first image data D11 to the side of the left end part of the first image data D11. In other words, when the tendency of the mammary glands to be located near the nipple is reflected in the first image data D11, the brightness value of the first image data D11 does not need to decrease monotonically as described above.

Second Image Data D12

As shown in FIGS. 12 and 15, the second image data D12 is image data in which the brightness value of each human body pixel in mammography image D0 is corrected so that the brightness value of the human body pixel in the mammography image D0 changes in the vertical direction of the mammography image D0. In the third embodiment, the brightness value of each human body pixel of the second image data is based on the second direction between the position (coordinates) of the upper end of the left end (upper left corner) in mammography image D0 and each human body pixel in human body area Rg1. That is, the second image data D12 is the image data in which the brightness value of each human body pixel in the mammography image D0 is corrected so that the brightness value of the human body pixel in mammography image D0 changes according to the second direction distance between the upper end of the left end (upper left corner) in mammography image D0 and each human body pixel. The second direction is the direction that intersects the first direction. In the third embodiment, the second direction is the vertical direction. Therefore, in the third embodiment, the first and second directions are orthogonal to one another. The first and second directions do not have to be orthogonal to one another.

In the second image data D12 of the third embodiment, the brightness value of each human body pixel in the mammography image D0 is corrected so that the brightness value of each human body pixel increases as the second direction distance increases. In other words, since the second direction distance is the smallest at the upper end of the left end (upper left corner) of the second image data D12, the brightness value of the upper end of the left end of the second image data D12 is the smallest. Also, since the lower end of the left end (lower left corner) of the second image data D12 has the maximum second direction distance, the brightness value of the human body pixel of this lower end of the left end is the maximum Furthermore, the brightness value of the human body pixel increases monotonically from a side of the upper end of the left end of the second image data D12 to a side of the lower end of the left end. The brightness value of the human body pixel may or may not decrease in proportion to this second direction distance. Further, in the third embodiment, the gradation value of the human body pixel at the upper end of the left end of the second image data D12 is 0, and the gradation value of the human body pixel at the lower end of the left end of the second image data D12 is 1. The maximum and minimum values of brightness value are not limited to these values.

The position (coordinates) of the pixel whose brightness value is the median of the human body pixels of the second image data D12 matches the position (coordinates) of the pixel (the nipple pixel) of the nipple area RgN. Here, the median value is the brightness value in the middle of the order when the brightness values are arranged in descending order. In the third embodiment, the maximum value of the brightness value of the human body pixel of the second image data D12 is 1, and the minimum value is 0. Thus, the brightness value of the pixel whose brightness value is the median of the human body pixels of the second image data D12 is 0.5. Thus, in the third embodiment, the brightness value of each human body pixel in the mammography image D0 is corrected so that the brightness value of each human body pixel below the nipple area RgN is greater than the brightness value of each human body pixel above the nipple area RgN in the second image data D12. In the third embodiment, since the coordinates of the nipple area RgN are located at the central coordinates in the vertical direction, the brightness value at the uppermost coordinates in the vertical direction is 0, and the brightness value at the lowermost coordinates in the vertical direction is 1. However, the configuration of the third embodiment is not limited to this. For example, when the coordinates of the nipple area RgN are below the central coordinates in the vertical direction, the gradation value of the uppermost coordinates in the vertical direction is set to 0, and the gradation value of nipple area N is set to 0.5. As a result, the gradation value of 1 or less is appropriately assigned to the gradation value of the lowermost coordinate in the vertical direction. Conversely, when the coordinates of the nipple area RgN are above the central coordinates in the vertical direction in the mammography image D0, the gradation value of the lowermost coordinates in the vertical direction is set to 1, and the gradation value of the nipple area RgN is set to 0.5.

Figure 18A:
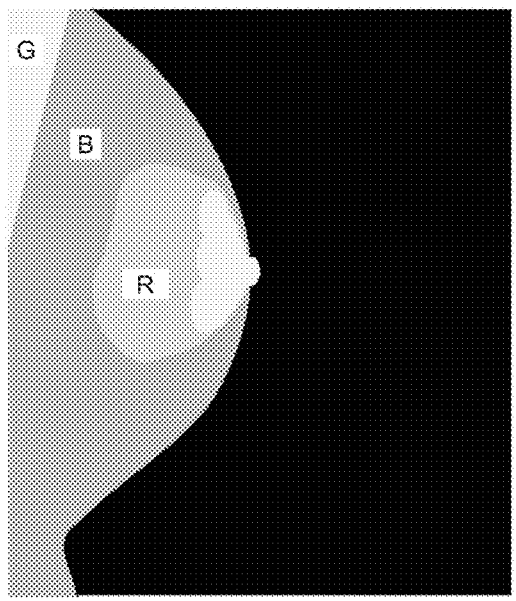
FIG. 18A is an example of the mammography image.
Figure 18B:
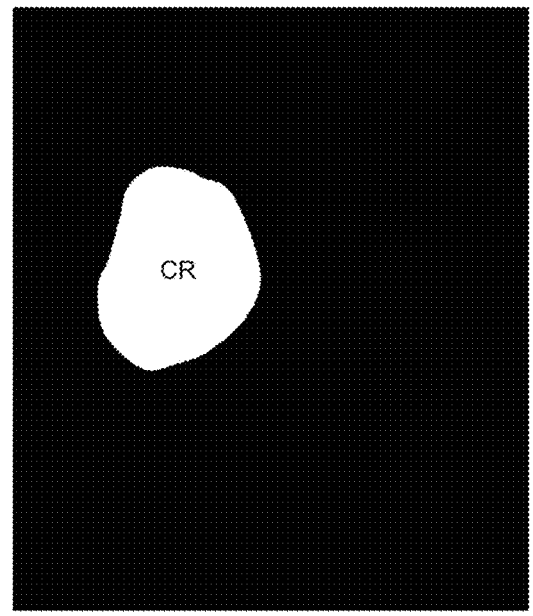
FIG. 18B is an example of correct data showing a position of the mammary gland in the mammography image shown in FIG. 18A.

Effects of the first additional data D1 will be explained using FIGS. 18A to 18D. FIG. 18A schematically shows mammography image D0. FIG. 18B schematically shows the correct answer data corresponding to the mammography image shown in FIG. 18A. An area CR in FIG. 18B shows, for example, the pixels, which are determined as the mammary gland by the doctor.

Figure 18C:
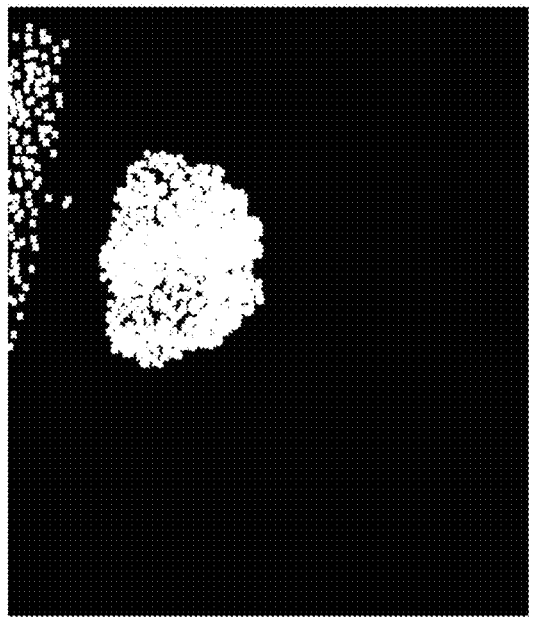
FIG. 18C is a schematic diagram showing the candidate pixel map when learning based on the first additional data is not performed.
Figure 18D:
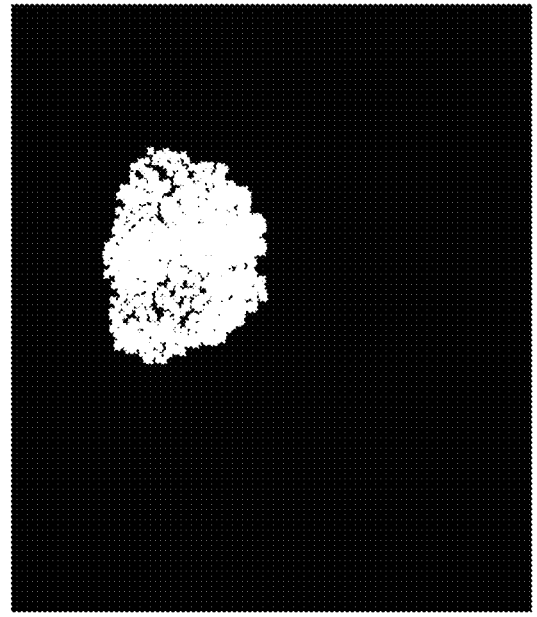
FIG. 18D is, as explained in the third embodiment, a schematic diagram showing the candidate pixel map when learning is performed based on the first additional data.

When the mammary gland area extractor 3 is trained without using the first additional data, the mammary gland area extractor 3 may generate the candidate pixel map as shown in FIG. 18C. In FIG. 18C, the white spots represent pixels (the candidate pixels) whose probability P exceeds the first threshold. When the mammary gland area extractor 3 is trained without using the first additional data, a large number of the candidate pixels are generated in the pectoralis major muscle area as well as in the area corresponding to the area CR of FIG. 18B, as shown in FIG. 18C. The fact that a large number of the candidate pixels are also generated in the pectoralis major muscle area indicates that the accuracy of the candidate pixel map is low. The low accuracy of the candidate pixel map means that the accuracy of the probability map is also low. Furthermore, the low accuracy of the candidate pixel map causes a decrease in the accuracy of the mammary gland area map, the accuracy of the mammary gland pixel map, and the accuracy of calculating the mammary gland density. On the other hand, when the mammary gland area extractor 3 is trained using the first additional data, the mammary gland area extractor 3 can generate the candidate pixel map as shown in FIG. 18D. In the candidate pixel map shown in FIG. 18D, the candidate pixel is generated in the area corresponding to the area CR of FIG. 18B, while the generation of the candidate pixel is suppressed in the pectoralis major muscle area. When the mammary gland area extractor 3 is trained using the first additional data, the accuracy of the candidate pixel map is high, so the accuracy of the probability map is also high. Besides, the high accuracy of the candidate pixel map makes the accuracy of the mammary gland area map, the accuracy of the mammary gland pixel map, and the accuracy of calculating the mammary gland density higher, <Second Additional Data>

In the mammography images, the window level adjustment is performed based on the following viewpoints for example.

From the first point of view, when the mammary gland concentration is high, the area around the mammary gland in the mammography image becomes white and blurry. Thus the window level of the mammography image is adjusted so that the mammography image overall is made darker, thereby allowing the observers to recognize the details of the mammary gland.

From the second viewpoint, when the mammary gland concentration is low, the window level of the mammography image is adjusted so that the mammography image overall is made brighter to the extent that the observers can recognize the fat, thereby allowing the observers to recognize the details of both the mammary gland and the fat.

When a lot of learning is done with the mammography image adjusted based on the first viewpoint and the weight coefficients are fixed, information processing devices may not provide an accurate output (the probability map) with a patient corresponding to the mammography image adjusted based on the second viewpoint and vice versa. In other words, there is a variation in window adjustment depending on the mammary gland concentration, and as a result, the accuracy of the probability map may be reduced. Therefore, in the third embodiment, the mammary gland area extractor 3 is trained by using the brightness value (representative brightness value) which is a representative of the mammography image or the image data that reflects on the distribution of the brightness value of the mammography image, thus making the output (the probability map) of the mammary gland area extractor 3 more accurate.

Figure 16:
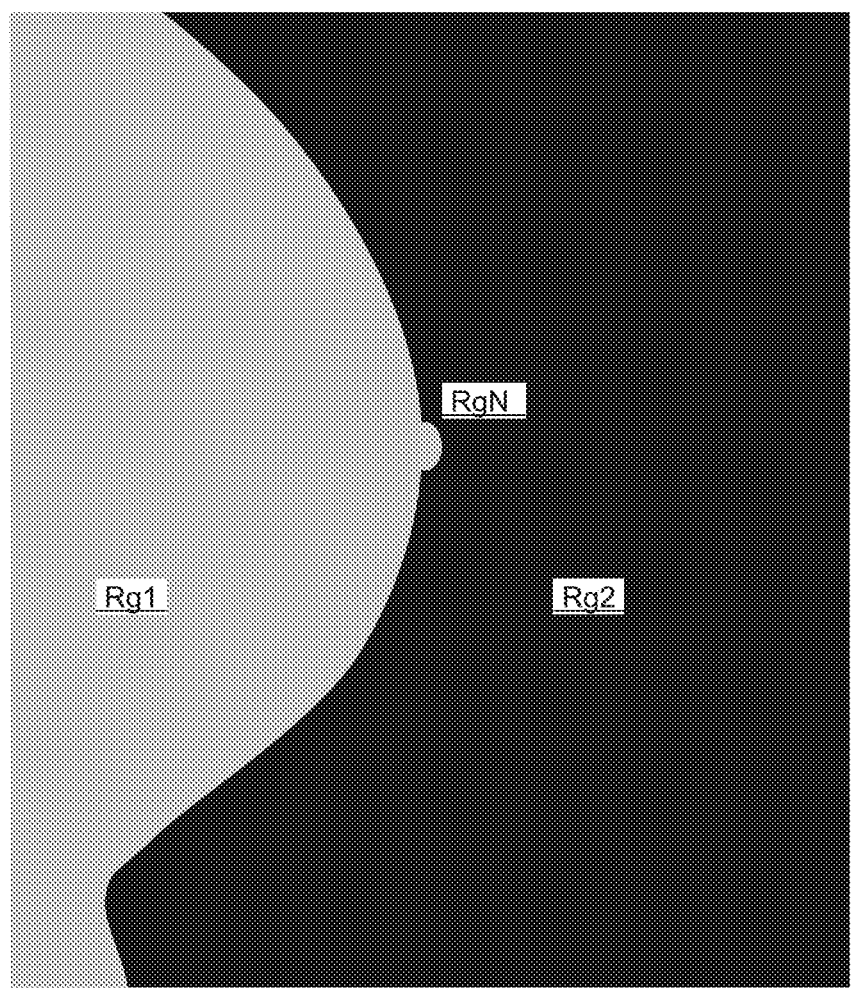
FIG. 16 is a schematic diagram showing an example of second additional data.

As shown in FIGS. 12 and 16, the second additional data is data indicating the representative brightness value of the mammography image D0 or the distribution of the brightness value of the mammography image D0. More specifically, the second additional data is image data in which the brightness value of all human body pixels in mammography image D0 is corrected based on the representative brightness value or the distribution. The brightness values of all human body pixels in the second additional data are the same. Here, the average value, the mode value, or the median value can be used as the representative brightness value. The average value is the sum of the brightness values of all human body pixels divided by the number of all human body pixels. The mode value is the brightness value that appears most frequently among the brightness values of all human body pixels. The median value is the brightness value corresponding to the middle of the order when the brightness values of all human body pixels are arranged in descending order. Further, the second additional data may be data indicating the distribution of brightness values, and may be, for example, a histogram indicating the distribution of the brightness values of all human body pixels. When the histogram is used in the third embodiment, it is preferable that the mammary gland area probability calculator 7 is provided with a sequential propagation type neural network. That is, the mammary gland area probability calculator 7 is configured to output the probability P based on a learning model that outputs the probability P by inputting, for example, the brightness value of each pixel of the mammography image D0 and the frequency of the histogram at each brightness value into the sequential propagation type neural network.

In the third embodiment, all of the training data are image data. That is, the mammography image D0, the first and second additional data D1 and D2 are image data. Since the first additional data D1 is data that reflects on the distance between the nipple and each pixel, the mammary gland area extractor 3 performs the learning that reflects on the coordinates. For this reason, the mammary gland area extractor 3 enables more accurate output. Note that the second additional data does not necessarily have to be image data. Even when the mammary gland area extractor 3 performs the learning based on the data indicating the above-mentioned representative brightness value and the distribution, it is expected that the output of the mammary gland area extractor 3 can be accurate.

3-2. Pre-Processor 6

The pre-processor 6 is configured to extract the human body area Rg1 in the process of the noise removal step described in the first embodiment and is configured to generate image data DRg1. The human body area extraction by the pre-processor 6 will be described.

The pre-processor 6 extracts the human body area Rg1 from the mammography image D0. Here, the human body area Rg1 tends to be brighter than the non-human body area Rg2. The pre-processor 6 uses this tendency to extract the human body area Rg1 from the mammography image D0. Then, pre-processor 6 generates the image data DRg1 by extracting the human body area Rg1. The image data DRg1 is used to generate the first and second additional data D1 and D2.

The flow in which the pre-processor 6 extracts the human body area Rg1 and generates the image data DRg1 is explained with reference to FIG. 17. The pre-processor 6 assigns 1 to each pixel of the mammography image D0 that has the brightness value equal to or higher than a set threshold, and assigns 0 to each pixel of the mammography image D0 that has the brightness value less than the set threshold (step S1). Here, the assigned values such as 1 and 0 are merely convenient numerical values for distinguishing the brightness of the pixels, and are not limited to these. Also, the set threshold is variable. In the pre-processor 6, the set threshold is set high at the beginning of the flow for extracting the human body area Rg1, and the set threshold is gradually set low as described later.

The pre-processor 6 counts the number of pixels having the brightness value equal to or higher than the set threshold among the pixels of the mammography image D0 (step S2). Then, the pre-processor 6 calculates a ratio x of the counted number to the total number of pixels of the mammography image D0 (step S3). The pre-processor 6 determines whether the calculated ratio x is a predetermined ratio pt (for example, 40%) (step S4). Although the ratio is set to the predetermined value pt here for convenience, the pre-processor 6 may determine whether the calculated ratio x is in a predetermined range. When this calculated ratio x is not a predetermined ratio pt, that is, when the calculated ratio x is higher than the predetermined ratio pt, the pre-processor 6 decreases the set threshold (step S5). The amount of decrease in the set threshold may be predetermined, for example. Then, the processing performed on the pre-processor 6 is returned to step S1. Further, when the calculated ratio x is the predetermined ratio pt, the pre-processor 6 determines that the pixel to which 1 is assigned in step S1 is the human body area Rg1 (step S6). The pre-processor 6 generates the image data DRg1 indicating the human body area Rg1 extracted from the mammography image D0 (step S7). The image data DRg1 has data indicating the human body area Rg1 and data regarding the brightness value of each pixel of the human body area Rg1.

3-3. Mammary Gland Area Extractor 3

Figure 10:
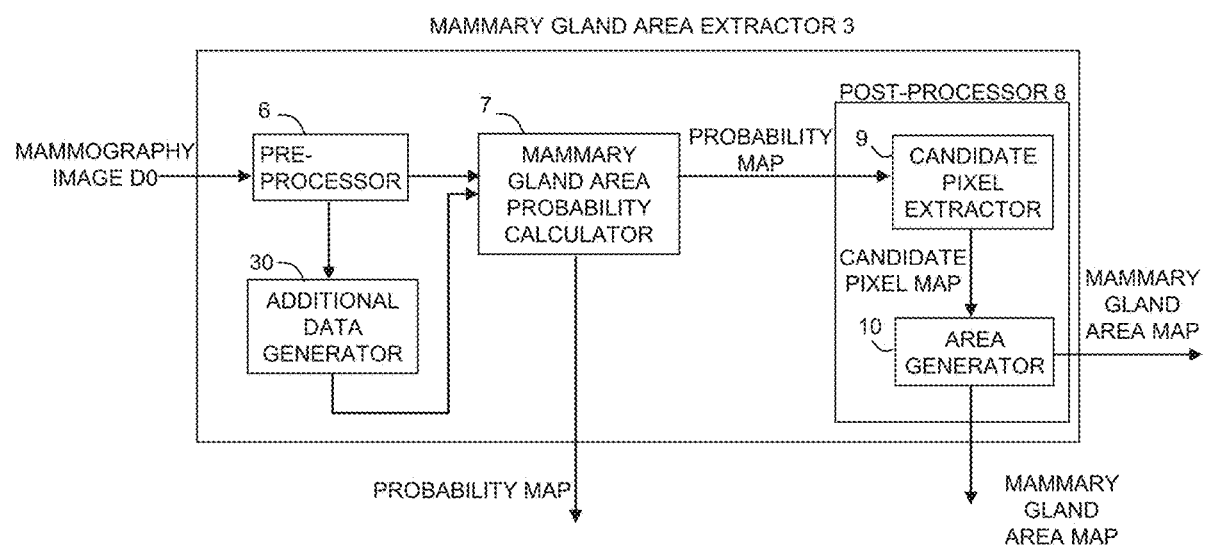
FIG. 10 is a block diagram showing a configuration of the mammary gland area extractor 3 according to the third embodiment of the present invention.

As shown in FIG. 10, the mammary gland area extractor 3 includes an additional data generator 30 in addition to the configuration of the first embodiment.

<Additional Data Generator 30>

Figure 11A:
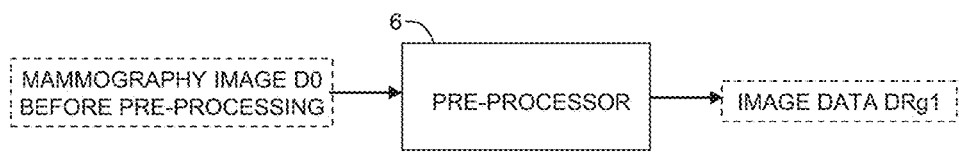
FIG. 11A is a block diagram showing a detailed configuration of a pre-processor 6 in FIG. 10.
Figure 11B:
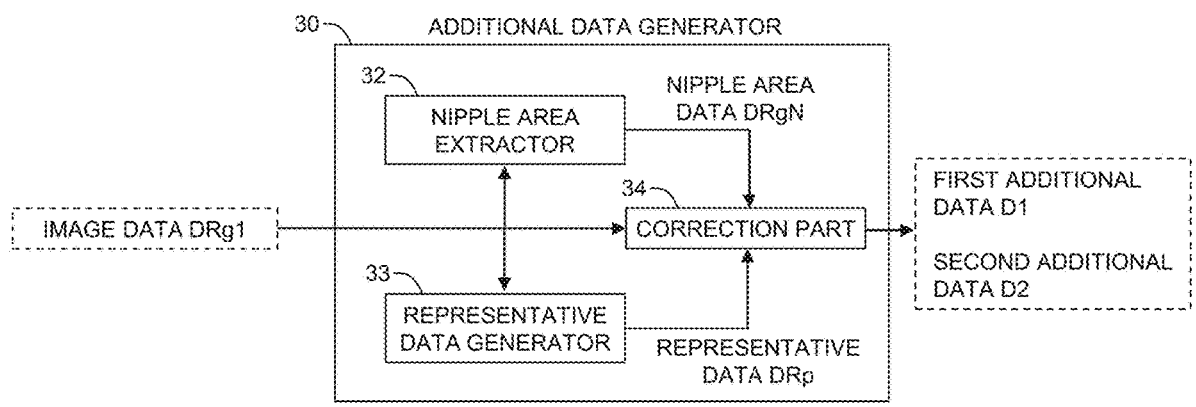
FIG. 11B is a block diagram showing a detailed configuration of an additional data generator 30 in FIG. 10.

As shown in FIG. 11B, the additional data generator 30 is configured to generate the first and second additional data D1 and D2. The additional data generator 30 has a nipple area extractor 32, a representative data generator 33, and a correction part 34.

Nipple Area Extractor 32

The nipple area extractor 32 is configured to extract (detects) the position (coordinates) of the nipple area RgN based on the image data DRg1. Then, the nipple area extractor 32 generates nipple area data DRgN indicating the position (coordinates) of the nipple area RgN. In the image data DRg1, the nipple is the most protruding part. The nipple area extractor 32 uses this feature of the nipple to extract the nipple area RgN from the image data DRg1.

Figure 13:
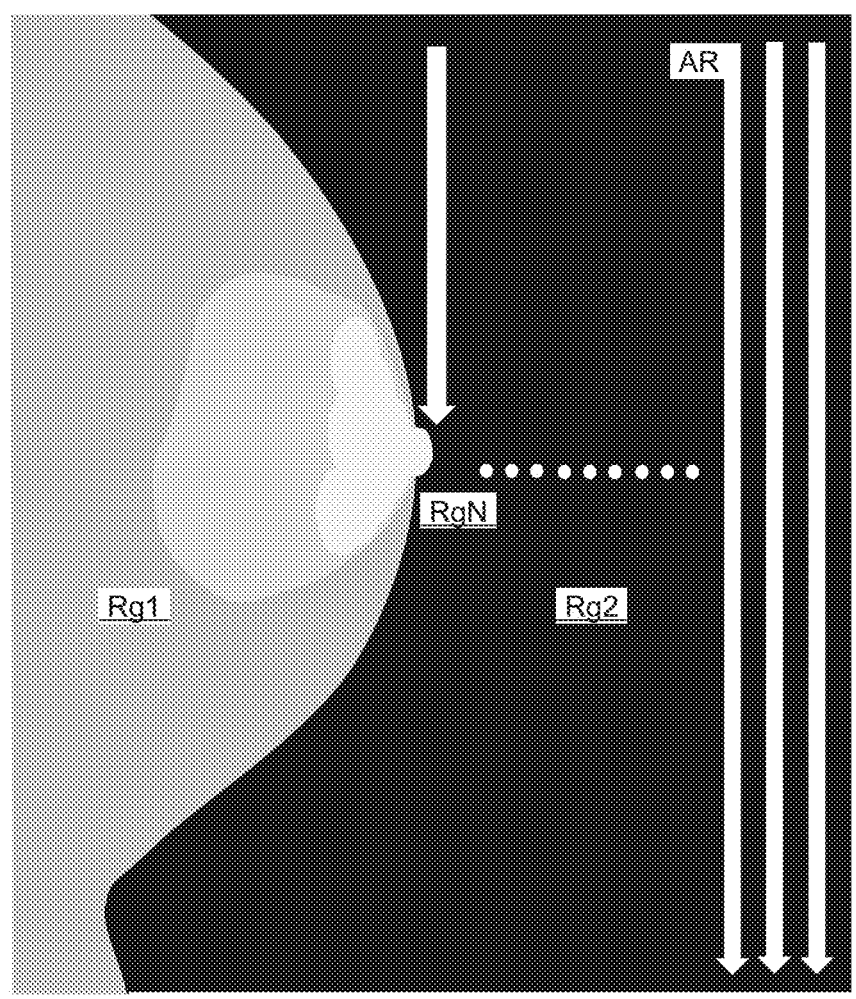
FIG. 13 is a schematic diagram showing the pixels, in the mammography image shown in FIG. 12, which are divided into a human body area Rg1 and a non-human body area Rg2.

As shown in FIG. 13, the nipple area extractor 32 scans the brightness value of each pixel of the mammography image D0 in the vertical direction. In FIG. 13, the arrow AR indicates the scanning direction. When the nipple area extractor 32 completes scanning the brightness value of the pixels in one row in the vertical direction, the nipple area extractor 32 sequentially scans the brightness value of the pixels in the adjacent row. Then, the nipple area extractor 32 determines the pixel, whose brightness value has been equal to or higher than the predetermined brightness value, as the nipple area RgN for the first time since the nipple area extractor 32 starts the scanning. The method of extracting the position of the nipple area RgN is not limited to this.

Representative Data Generator 33

The representative data generator 33 is configured to acquire representative data DRp to generate the second additional data. The representative data DRp is the data indicating the representative brightness value of the mammography image D0 or the distribution of the brightness value of the mammography image D0, described above. Here, the case, where the representative data DRp is the average value of the representative brightness value, will be described as an example. The representative data generator 33 calculates the sum of the brightness values of each pixel of the human body area Rg1 determined by the pre-processor 6. Then, the representative data generator 33 can acquire the average value by dividing this sum by the number of pixels of the human body area Rg1 determined by the pre-processor 6.

Correction Part 34

As shown in FIG. 11B, the correction part 34 is configured to correct the mammography image D0 based on the human body area Rg1 (the image data DRg1) determined by the pre-processor 6 and the nipple area RgN (the nipple area data DRgN) determined by the nipple area extractor 32, and is configured to generate the first additional data D1.

In addition, the correction part 34 is configured to correct the mammography image D0 based on the human body area Rg1 (the image data DRg1) determined by the pre-processor 6 and the representative data DRp acquired by the representative data generator 33, and is configured to generate the second additional data D2.

<Mammary Gland Area Probability Calculator 7>

The mammary gland area probability calculator 7 is configured to calculate the probability P of the mammary gland area R in mammography image D0. In the third embodiment, the probability P is calculated based on the learning model that outputs the probability P when the mammography image D0, the first and second additional data D1 and D2 are input.

In the third embodiment, the input data of the training data are the mammography image D0, the first and second additional data D1 and D2. The correct answer data is data in which the values of the pixels in the area, which are determined as the mammary gland area by the doctor, are set to 1, and the values of the other pixels are set to 0. A large number of the training data and the correct answer data are input to the information processing device 1. In this process, the mammary gland area probability calculator 7 changes the weight coefficient of the filter as appropriate, and the mammary gland area probability calculator 7 finally determines this weight coefficient.

At the stage where the information processing device 1 is used for the diagnosis of the patient (hereinafter referred to as the operation stage), the mammography image D0 of the patient is input to the mammary gland area probability calculator 7. As a result, the additional data generator 30 generates the first and second additional data D1 and D2 from the mammography image D0. Then, the mammary gland area probability calculator 7 processes the mammography image D0, the first and second additional data D1 and D2 based on the determined weighting coefficient, and outputs the probability map.

In the operation stage, the process of removing the pectoralis major muscle area G (noise) by the pre-processor 6 becomes unnecessary. the mammary gland area probability calculator 7 has trained based on the first additional data. Thus, even when the mammography image including the pectoralis major muscle area G is input to the mammary gland area probability calculator 7, the mammary gland area probability calculator 7 more reliably calculates the probability P of the pixel lower in the pectoralis major muscle area G.

3-4. Modified Embodiment of Third Embodiment

Figure 19:
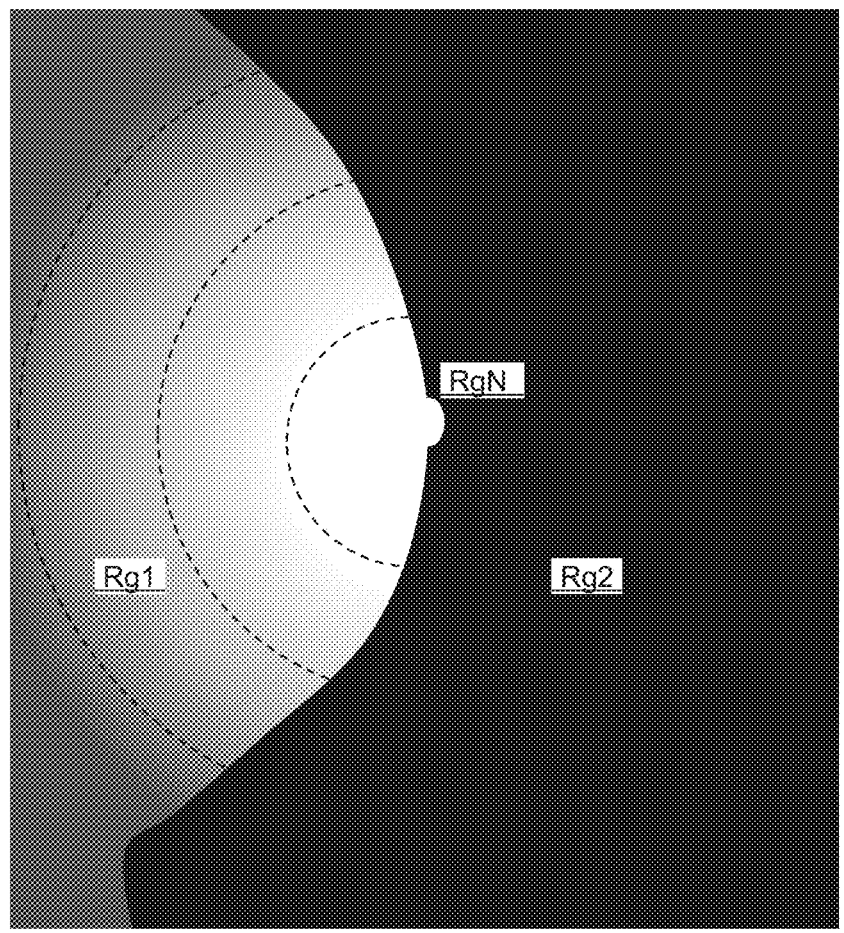
FIG. 19 is a schematic diagram showing an example of the first additional data related to a modified example.

The configuration of the first additional data D1 is not limited to the configuration having the first image data D11 and the second image data D12. As shown in FIG. 19, the first additional data D1 may include image data only in the configuration centered on the nipple area RgN instead of the first image data D11 and the second image data D12. In the image data related to the modified embodiment, the brightness value of each human body pixel in the mammography image D0 is corrected so that the brightness value of each human body pixel increases as the linear distance from the nipple area RgN to each human body pixel decreases.

Further, in the third embodiment, the mammary gland area probability calculator 7 is configured to perform the learning using the first additional data D1 and the second additional data in addition to the mammography image D0, but the present invention is not limited to this. The mammary gland area probability calculator 7 may be configured to perform the learning using one of the first and second additional data D1 and D2 in addition to the mammography image D0. In this case, in the operation stage, the additional data generator 30 generates one of the first and second additional data D1 and D2 from the mammography image D0. Then, the mammary gland area probability calculator 7 outputs the probability map based on the mammography image D0 and one of the first and second additional data D1 and D2.

Figure 20:
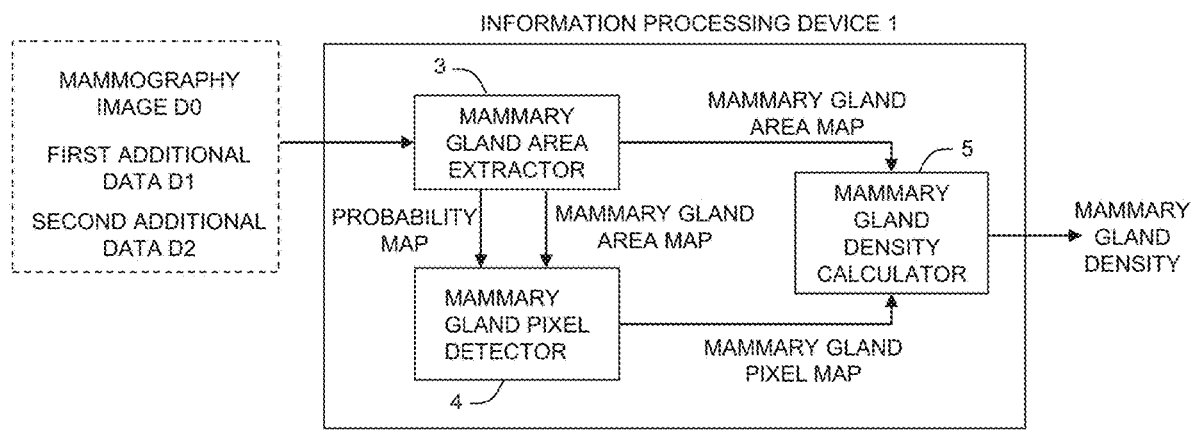
FIG. 20 is a block diagram showing a configuration of information processing device 1 according to a modified example.

In the third embodiment, the information processing device 1 includes the additional data generator 30, but the information processing device 1 is not limited to this. The additional data generator 30 may be provided outside the information processing device 1. As shown in FIG. 20, in this case, the mammography image D0 and pre-generated first additional data D1 and second additional data D2 are input to the information processing device 1.

Further, in the third embodiment, the human body area Rg1 is arranged on the left side in the mammography image D0, but the arrangement is not limited to this. If the arrangement of the human body area Rg1 of the image data at the time of the learning stage and the arrangement of the human body area Rg1 of the image data at the time of the operation stage are aligned, the arrangement of the human body area Rg1 may be, for example, symmetrical with the arrangement shown in FIG. 12.

In the third embodiment, the first additional data is image data, but the first additional data is not limited to this. The first additional data may be, for example, the position data of the nipple. In this case, the additional data generator 30 generates image data based on the position data of the nipple.

Further, the first additional data may reflect on the position data of the human body area Rg1 or the position data of the pectoralis major muscle in addition to the position data of the nipple. The additional data generator 30 may use, for example, a function or a table, in which the output (for example, brightness value) changes from the position of the nipple toward the position of the human body area Rg1 or the position of the pectoralis major muscle, and generate image data. The mammary gland area probability calculator 7 can perform the learning using the image data generated in this way, and can also output the probability P at the operation stage.

The image data related to the first additional data is the image data in which the pixel value of the human body pixel in the mammography image D0 is corrected based on the position of the nipple pixel in the mammography image. As described above, the pixel value may be the brightness value of the human body pixel in the mammography image, and may not be the brightness value of the human body pixel in the mammography image. For example, when generating the image data related to the first additional data using the coordinates of the nipple and the coordinates of the human body area Rg1 or the pectoralis major muscle, the information processing device 1 can generate the image data related to the first additional data without using the brightness value of the human body pixel in the mammography image. Further, the second additional data may also be, for example, the image data in which the pixel value of the human body pixel in mammography image D0 is corrected.

Figure 21A:
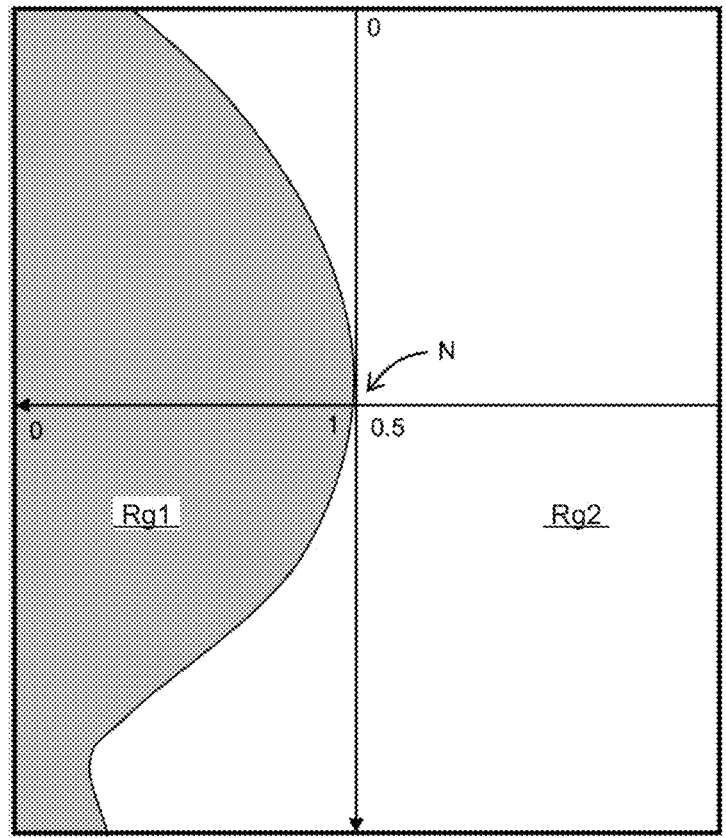
FIG. 21A is an explanatory diagram schematically showing a coordinate system of the third embodiment.
Figure 21B:
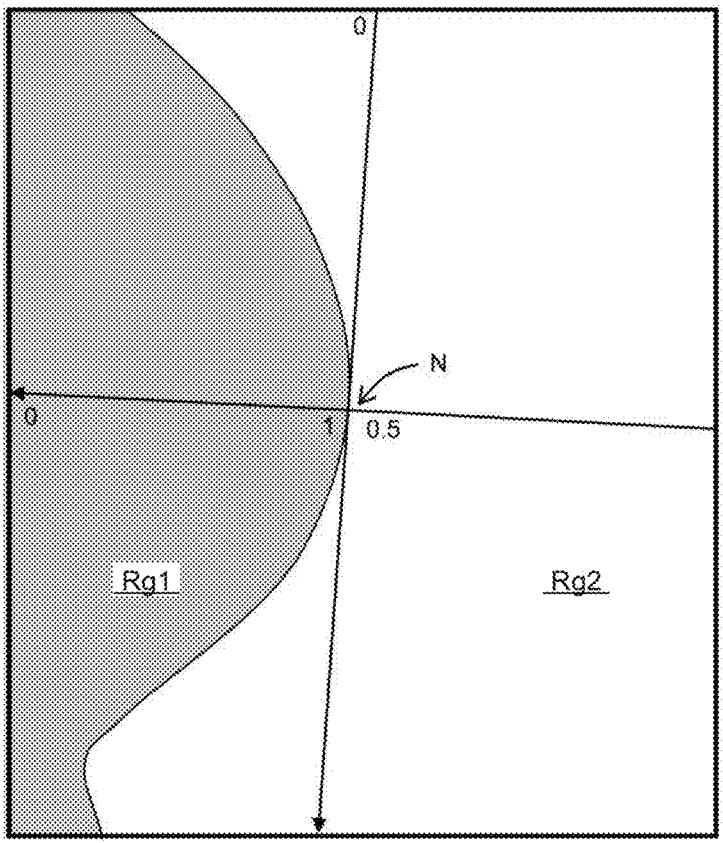
FIG. 21B is an explanatory diagram schematically showing the coordinate system according to a modified example.

In the third embodiment, the coordinate system of the first additional data is a cartesian coordinate system centered on the nipple area N, as shown in FIG. 21A. That is, in the coordinate system of the third embodiment, the vertical axis is parallel in the vertical direction, the horizontal axis is parallel in the horizontal direction, and the intersection of the vertical axis and the horizontal axis is the nipple area N. Here, the coordinate system of the first additional data is not limited to this. As shown in FIG. 21B, the tangent line passing through the edge of the human body area Rg1 may be the vertical axis, and the line orthogonal to the vertical axis may be the horizontal axis. Here, the tangent line passing through the edge of the human body area Rg1 is the tangent line in the nipple area N. Also, the edge of the human body area Rg1 is the breast curve, which corresponds to the boundary between the human body area Rg1 and the non-human body area Rg2.

4. Other Embodiments

In the above embodiments, FCN is used as the learning model, but any sequential propagation type neural networks other than FCN can be used.

In the above embodiments, the probability P is calculated based on the learning model, but the probability P may be calculated based on the brightness value of a small area including each pixel or a plurality of pixels. For example, the probability P may be calculated based on the histogram of the brightness value, or the probability P may be calculated based on the absolute value of the brightness value or the difference of the brightness values of the peripheral pixels.

In the above embodiments, the mammary gland area is extracted based on the probability P. However, instead of using the probability P, the mammary gland area may be extracted using a method of directly obtaining the mammary gland area based on the magnitude of the brightness value or a method of determining whether it is a mammary gland area based on the transition of the brightness value in the horizontal direction/vertical direction In the above embodiments, the probability, that the pixel is the mammary gland area in the mammography image, is calculated for each pixel, but the probability, that the pixel is the mammary gland area in the mammography image, may be calculated for each small area including a plurality of pixels.

In the above embodiments, the information processing device 1 includes the mammary gland area extractor 3, the mammary gland pixel detector 4, and the mammary gland density calculator 5, but the embodiments are not limited to this. For example, in the first and second embodiments, the information processing device 1 includes the mammary gland area probability calculator 7 of the mammary gland area extractor 3, and the post-processor 8 of the mammary gland area extractor 3, the mammary gland pixel detector 4, and the mammary gland density calculator 5 may be provided outside the information processing device 1. Further, in the third embodiment, the information processing device 1 includes the mammary gland area probability calculator 7 of the mammary gland area extractor 3 and the additional data generator 30 of the mammary gland area extractor 3, and the post-processor 8 of the mammary gland area extractor 3, the mammary gland pixel detector 4, and the mammary gland density calculator 5 may be provided outside the information processing device 1. In these cases, the information processing device 1 generates the probability map, and the generated probability map can be used outside of the information processing device 1.

That is, the embodiments may provide an information processing device comprising a mammary gland area extractor, wherein the mammary gland area extractor is configured to extract a mammary gland area in a mammography image, the mammary gland area extractor includes a mammary gland area probability calculator, the mammary gland area probability calculator is configured to calculate a probability based on a learning model that outputs the probability when the mammography image is input.

Further, the embodiments may also provide an information processing device comprising a mammary gland area extractor, wherein the mammary gland area extractor is configured to extract a mammary gland area in a mammography image, the mammary gland area extractor includes a mammary gland area probability calculator, the mammary gland area probability calculator is configured to calculate a probability based on a learning model that outputs the probability when at least one of first and second additional data in addition to the mammography image are input.

Besides, the information processing device may use the learning model that outputs the probability when the mammography image and first additional data are input, or may use the learning model that output the probability when the mammography image and the second additional data are input. For example, when the information processing device is trained using the mammography image with an adjusted window level, the information processing device may use the learning model that outputs the probability when the mammography image and the first additional data are input. Besides, in the case that the pectoralis major muscle area is removed in advance, or in the case that the learning model is sufficiently trained so that the candidate pixel is not generated in the area corresponding to the pectoralis major muscle area as the first embodiment, the information processing device may use the learning model that outputs the probability when the mammography image and the second additional data are input.

Even these embodiments can obtain the same effect as the embodiments described above.

DESCRIPTION OF REFERENCE SIGNS

1: information processing device
3: mammary gland area extractor
4: mammary gland pixel detector
5: mammary gland density calculator
6: pre-processor
7: mammary gland area probability calculator
8: post-processor
9: candidate pixel extractor
10: area generator
11: mammary gland area image extractor
12: brightness determination part
30: additional data generator
32: nipple area extractor
33: representative data generator
34: correction part
D0: mammography image
D1: first additional data
D11: first image data
D12: second image data
D2: second additional data
DRg1: image data
DRgN: nipple area data
DRp: representative data
Rg1: human body area
Rg2: non-human body area
RgN: nipple area
B: mammary area
G: pectoralis major muscle area
R: mammary gland area

The invention claimed is:

1. An information processing device comprising:
a mammary gland area extractor configured to extract a mammary gland area in a mammography image, wherein the mammary gland area extractor comprises:
a mammary gland area probability calculator configured to calculate a probability that an area in the mammography image is the mammary gland area; and
a post-processor configured to extract the mammary gland area based on the probability;
a mammary gland pixel detector configured to detect a mammary gland pixel in the mammary gland area; and
a mammary gland density calculator configured to calculate a mammary gland density based on a ratio of the mammary gland pixels to the mammary gland area, wherein the mammary gland area is a narrower area than an entire breast in the mammography image.

2. The information processing device of claim 1, wherein the post-processor further comprises:
a candidate pixel extractor configured to generate a candidate pixel map by extracting, as a candidate pixel, a pixel having the probability that is equal to or greater than a first threshold; and
an area generator configured to form the mammary gland area by filling in a missing area with respect to the candidate pixel map.

3. The information processing device of claim 1, wherein the mammary gland area probability calculator is further configured to calculate the probability based on a learning model that outputs the probability when the mammography image is input.

4. The information processing device of claim 3, wherein the learning model is trained outside the information processing device in advance.

5. The information processing device of claim 3, wherein the learning model is configured to be trainable in the information processing device.

6. The information processing device of claim 1, wherein the mammary gland area probability calculator is further configured to calculate the probability based on a learning model that outputs the probability when the mammography image and first additional data are input, and
the first additional data is data relating to a position of a nipple in the mammography image.

7. The information processing device of claim 6, wherein the first additional data is image data in which a pixel value of a human body pixel in the mammography image is corrected based on a position of a nipple pixel in the mammography image.

8. The information processing device of claim 7, wherein the first additional data is the image data in which the pixel value of the human body pixel in the mammography image is corrected so that the pixel value of the human body pixel in the mammography image changes according to a linear distance between the nipple pixel and the human body pixel.

9. The information processing device of claim 8, wherein the first additional data is the image data in which the pixel value of the human body pixel in the mammography image is corrected so that the pixel value of the human body pixel increases as the linear distance between the nipple pixel and the human body pixel decreases.

10. The information processing device of claim 7, wherein the first additional data further comprises:
first image data in which the pixel value of the human body pixel in the mammography image is corrected so that the pixel value of the human body pixel in the mammography image changes in a first direction of the mammography image second image data in which the pixel value of the human body pixel in the mammography image is corrected so that the pixel value of the human body pixel in the mammography image changes in a second direction of the mammography image, and the first direction and the second direction cross.

11. The information processing device of claim 10, wherein the first additional data is the image data in which the pixel value of the human body pixel in the mammography image is corrected so that the pixel value of the human body pixel increases as the linear distance in the first direction between the nipple pixel and the human body pixel decreases, and the second additional data is the image data in which the pixel value of the human body pixel in the mammography image is corrected so that the pixel value of the human body pixel increases from an upper side in the second direction to a lower side in the second direction.

12. The information processing device of claim 1, wherein the mammary gland area probability calculator is further configured to calculate the probability based on a learning model that outputs the probability when the mammography image and second additional data are input, and the second additional data is data indicating distribution of representative brightness value of the mammography image or brightness value of the mammography image.

13. The information processing device of claim 12, wherein the second additional data is image data in which the brightness value of a human body pixel in the mammography image is corrected based on the representative brightness value or the distribution.

14. The information processing device of claim 1, wherein the mammary gland area probability calculator is further configured to calculate the probability without removing a pectoralis major muscle area in the mammography image.

15. The information processing device of claim 1, wherein the mammary gland pixel detector is further configured to detect the mammary gland pixel in the mammary gland area based on the probability.

16. The information processing device of claim 15, wherein the mammary gland pixel detector is further configured to detect a pixel, as the mammary gland pixel, having the probability that is equal to or greater than a second threshold, and the probability of the mammary gland area is higher when the second threshold is used than when the first threshold is used.

17. The information processing device of claim 1, wherein the mammary gland pixel detector is further configured to detect the mammary gland pixel based on a brightness value of the mammary gland area.

18. An information processing method comprising:
    calculating a probability that an area in a mammography image is a mammary gland area in the mammography image;
    extracting the mammary gland area in the mammography image based on the probability;
    detecting a mammary gland pixel in the mammary gland area; and
    calculating a ratio of the mammary gland pixels to the mammary gland area, wherein the mammary gland area is a narrower area than an entire breast in the mammography image.

19. A non-transitory computer readable medium that stores a computer program causing a computer to execute an information processing method, the information processing method comprising:
    calculating a probability that an area in a mammography image is a mammary gland area in the mammography image;
    extracting the mammary gland area in the mammography image based on the probability;
    detecting a mammary gland pixel in the mammary gland area; and
    calculating a ratio of the mammary gland pixels to the mammary gland area, wherein the mammary gland area is a narrower area than an entire breast in the mammography image.

* * * * *